US012797649B2

(12) United States Patent
Chan et al.

(10) Patent No.: US 12,797,649 B2
(45) Date of Patent: Nov. 17, 2026

(54) RESPIRATOR AND AIR PURIFICATION SYSTEM

(71) Applicant: RHT LIMITED, Hong Kong (CN)

(72) Inventors: Rudy Chi Keung Chan, Hong Kong (CN); Ka Wai Jim, Hong Kong (CN)

(73) Assignee: RHT LIMITED, Hong Kong (CN)

( * ) Notice: Subject to any disclaimer, the term of this patent is extended or adjusted under 35 U.S.C. 154(b) by 718 days.

(21) Appl. No.: 18/250,985

(22) PCT Filed: Oct. 27, 2021

(86) PCT No.: PCT/CN2021/126598
§ 371 (c)(1),
(2) Date: Apr. 28, 2023

(87) PCT Pub. No.: WO2022/089465
PCT Pub. Date: May 5, 2022

(65) Prior Publication Data

US 2023/0381551 A1 Nov. 30, 2023

Related U.S. Application Data

(60) Provisional application No. 63/198,651, filed on Nov. 1, 2020.

(51) Int. Cl.
*A62B 18/00* (2006.01)
*A61L 9/015* (2006.01)
(Continued)

(52) U.S. Cl.
CPC ............ *A62B 18/006* (2013.01); *A61L 9/015* (2013.01); *A62B 7/10* (2013.01); *A62B 18/025* (2013.01);
(Continued)

(58) Field of Classification Search
CPC ......... A62B 7/10; A62B 18/00; A62B 18/003; A62B 18/006; A62B 18/025; A62B 23/00;
(Continued)

(56) References Cited

U.S. PATENT DOCUMENTS 4,244,937 A 1/1981 Durkin
4,673,416 A 6/1987 Sakakibara et al.
(Continued)

FOREIGN PATENT DOCUMENTS

CN 2317432 Y 5/1999
CN 1275436 A 12/2000
(Continued)

OTHER PUBLICATIONS

Machine translation of CN-106512246-A.*
(Continued)

*Primary Examiner* — Joseph D. Boecker
(74) *Attorney, Agent, or Firm* — EAGLE IP LIMITED

(57) ABSTRACT

A respirator (100) includes a face mask (130), a porous filter (230) comprising a filtration material, an air flow system (120) in fluid communication with the porous filter (230) and the face mask (130), and an oxidant generator (850) configured to produce at least one oxidant. The air flow system (120) includes an enclosed container (121) and a blower (310) housed within the enclosed container (121). The air flow system (120) is configured to generate a flow of air such that ambient air passes through the porous filter (230) to the face mask (130). At least one contaminant in the flow of air is adsorbed by the porous filter (230), and the filtration material catalyzes an oxidation reaction between the oxidant and the contaminant to promote decomposition of the contaminant on the porous filter (230). According to another aspect, provided is an air purification system includ-
(Continued)

ing at least one respirator (100) and a decontamination device (800).

10 Claims, 20 Drawing Sheets

(51) Int. Cl.

| | |
|---|---|
| ***A62B 7/10*** | (2006.01) |
| ***A62B 18/02*** | (2006.01) |
| ***A62B 19/02*** | (2006.01) |
| ***A62B 23/02*** | (2006.01) |
| ***F24F 8/26*** | (2021.01) |

(52) U.S. Cl.
CPC .............. *A62B 19/02* (2013.01); *A62B 23/02* (2013.01); *F24F 8/26* (2021.01)

(58) Field of Classification Search
CPC ......... A62B 23/02; A62B 19/02; A61L 9/015; A61L 9/22; F24F 8/26; F24F 3/16; A61M 15/02; A61M 2202/0216
See application file for complete search history.

(56) References Cited

U.S. PATENT DOCUMENTS

| | | | |
|---|---|---|---|
| 4,772,297 | A | 9/1988 | Anzai |
| 4,780,277 | A | 10/1988 | Tanaka et al. |
| 4,872,083 | A | 10/1989 | Blitshteyn |
| 5,141,906 | A | 8/1992 | Takeshima et al. |
| 5,221,520 | A | 6/1993 | Cornwell |
| 5,388,177 | A | 2/1995 | Ono et al. |
| 5,622,630 | A | 4/1997 | Romano |
| 5,685,895 | A | 11/1997 | Hagiwara et al. |
| 5,702,507 | A | 12/1997 | Wang |
| 5,835,840 | A | 11/1998 | Goswami |
| 5,843,288 | A | 12/1998 | Yamamoto |
| 5,885,546 | A | 3/1999 | Kumar et al. |
| 5,939,028 | A | 8/1999 | Bennett et al. |
| 5,961,919 | A | 10/1999 | Tachibana et al. |
| 6,120,584 | A | 9/2000 | Sakata et al. |
| 6,152,996 | A | 11/2000 | Linnersten et al. |
| 6,162,996 | A | 12/2000 | Schmidt et al. |
| 6,299,854 | B1 | 10/2001 | Henmi et al. |
| 6,358,374 | B1 | 3/2002 | Obee et al. |
| 6,489,259 | B2 | 12/2002 | LaBarge et al. |
| 6,607,702 | B1 | 8/2003 | Kang et al. |
| 6,887,438 | B2 | 5/2005 | Labarge et al. |
| 2002/0014071 | A1 | 2/2002 | Balmer et al. |
| 2002/0157661 | A1 | 10/2002 | Kornberger |
| 2003/0030374 | A1 | 2/2003 | Pai |
| 2006/0024217 | A1* | 2/2006 | Law ........................ F24F 8/192 422/186.04 |
| 2009/0014002 | A1 | 1/2009 | Krafthefer et al. |
| 2015/0202473 | A1 | 7/2015 | Curran et al. |
| 2017/0165445 | A1* | 6/2017 | Zereshkian .............. A62B 7/10 |
| 2017/0189727 | A1* | 7/2017 | Hunter ................. A62B 18/006 |
| 2017/0312557 | A1 | 11/2017 | Schuller |
| 2018/0104517 | A1 | 4/2018 | Schuller |
| 2020/0297962 | A1 | 9/2020 | Teng et al. |

FOREIGN PATENT DOCUMENTS

| | | | | | |
|---|---|---|---|---|---|
| CN | 1340679 | A | | 3/2002 | |
| CN | 102580537 | A | | 7/2012 | |
| CN | 103702690 | A | | 4/2014 | |
| CN | 204380019 | U | | 6/2015 | |
| CN | 205055237 | U | | 3/2016 | |
| CN | 205055238 | U | | 3/2016 | |
| CN | 105920929 | A | | 9/2016 | |
| CN | 106474639 | A | | 3/2017 | |
| CN | 106512246 | A | * | 3/2017 | ............... A62B 7/10 |
| CN | 107803226 | A | * | 3/2018 | .............. B01J 31/38 |
| CN | 207101657 | U | | 3/2018 | |
| CN | 111569287 | A | * | 8/2020 | ............. A61L 9/015 |
| DE | 202020105280 | U1 | * | 9/2020 | ............... A62B 7/10 |
| EP | 0616175 | A2 | | 9/1994 | |
| EP | 0950800 | A2 | | 10/1999 | |
| EP | 1905458 | A2 | | 4/2008 | |
| JP | S54104481 | A | | 8/1979 | |
| JP | H06327922 | A | | 11/1994 | |
| JP | H11137658 | A | | 5/1999 | |
| JP | H11221442 | A | | 8/1999 | |
| JP | 2001246227 | A | | 9/2001 | |
| RU | 1623346 | A3 | | 5/1998 | |
| TW | 491728 | B | | 6/2002 | |
| WO | WO-03092748 | A1 | * | 11/2003 | .............. A61L 9/16 |
| WO | 2020184993 | A1 | | 9/2020 | |

OTHER PUBLICATIONS

Machine translation of CN-107803226-A.*
Machine translation of CN-111569287-A.*
Machine translation of DE-202020105280-U1.*
Sen SE, Smith SM, Sullivan KA. Organic transformations using zeolites and zeotype materials. Tetrahedron. Oct. 29, 1999;55(44):12657-98.
Thomas JM, Raja R, Sankar G, Bell RG. Molecular-sieve catalysts for the selective oxidation of linear alkanes by molecular oxygen. Nature. Mar. 1999;398(6724):227-30.
Eliasson B, Kogelschatz U. Nonequilibrium volume plasma chemical processing. IEEE transactions on plasma science. Dec. 1991;19(6):1063-77.
Liu CJ, Vissokov GP, Jang BW. Catalyst preparation using plasma technologies. Catalysis Today. Mar. 15, 2002;72(3-4):173-84.
Francke KP, Miessner H, Rudolph R. Plasmacatalytic processes for environmental problems. Catalysis Today. Jun. 25, 2000;59(3-4):411-6.
Leichsenring S, Lenoir D, May HG, Kettrup A. Catalytic oxidation of chloromatic trace contaminations adsorbed on Wessalith Day by ozone. Chemosphere. Jul. 1, 1996;33(2):343-52.
Oda T, Kato T, Takahashi T, Shimizu K. Nitric oxide decomposition in air by using nonthermal plasma processing with additives and catalyst. IEEE Transactions on Industry Applications. Mar. 1998;34(2):268-72.
Yan K, Hui H, Cui M, Miao J, Wu X, Bao C, Li R. Corona induced non-thermal plasmas: fundamental study and industrial applications. Journal of electrostatics. Jul. 1, 1998;44(1-2):17-39.
Urashima K, Kostov KG, Chang JS, Okayasa Y, Iwaizumi T, Yoshimura K, Kato T. Removal of C/sub 2/F/sub 6/from a semiconductor process flue gas by a ferroelectric packed-bed barrier discharge reactor with an adsorber. IEEE Transactions on Industry Applications. Sep. 2001;37(5):1456-63.
Francke KP, Miessner H, Rudolph R. Cleaning of air streams from organic pollutants by plasma-catalytic oxidation. Plasma Chemistry and Plasma Processing. Sep. 2000;20(3):393-403.
Weitkamp J. Zeolites and catalysis. Solid state ionics. Jun. 1, 2000;131(1-2):175-88.
Zhu B, Li XS, Sun P, Liu JL, Ma XY, Zhu X, Zhu Am. A novel process of ozone catalytic oxidation for low concentration formaldehyde removal. Chinese Journal of Catalysis. Oct. 1, 2017;38(10):1759-69.
Zhang Y, Shi J, Fang W, Chen M, Zhang Z, Jiang Z, Shangguan W, Einaga H. Simultaneous catalytic elimination of formaldehyde and ozone over one-dimensional rod-like manganese dioxide at ambient temperature. Journal of Chemical Technology & Biotechnology. Jul. 2019;94(7):2305-17.
Fang R, Huang W, Huang H, Feng Q, He M, Ji J, Liu B, Leung DY. Efficient MnOx/SiO2@ AC catalyst for ozone-catalytic oxidation of gaseous benzene at ambient temperature. Applied Surface Science. Mar. 15, 2019;470:439-47.

* cited by examiner

RESPIRATOR AND AIR PURIFICATION SYSTEM

CROSS-REFERENCE TO RELATED APPLICATION

This application claims priority to, and the benefit of, U.S. Provisional Application having Ser. No. 63/198,651 filed on Nov. 1, 2020. The entire contents of the foregoing application are hereby incorporated by reference in its entirety for all purposes.

FIELD OF INVENTION

This invention relates to a respirator, and in particular a respirator utilizing one or more filters for purifying contaminated air.

BACKGROUND OF INVENTION

Personal protective equipment such as gas-masks and protective suits are useful to protect a user from a variety of harmful chemical or biological contaminants. However, these personal protective equipment are often designed for a single use for a limited period of time. Moreover, these personal protective equipment are prone to contamination, which are especially problematic and expensive to clean and dispose.

SUMMARY OF INVENTION

In the light of the foregoing background, it is an object of the present invention to provide an improved personal protection apparatus that can protect the user from contaminated air.

Accordingly, an exemplary embodiment is a respirator including a face mask, a porous filter comprising a filtration material, an air flow system in fluid communication with the porous filter and the face mask, and an oxidant generator configured to produce at least one oxidant. The air flow system includes an enclosed container and a blower housed within the enclosed container. The air flow system is configured to generate a flow of air such that ambient air passes through the porous filter to the face mask. At least one contaminant in the flow of air is adsorbed by the porous filter, and the filtration material catalyzes an oxidation reaction between the oxidant and the contaminant to promote decomposition of the contaminant on the porous filter.

According to another aspect, provided is an air purification system including at least one respirator and a decontamination device. The at least one respirator includes a face mask, a porous filter comprising a filtration material, and an air flow system in fluid communication with the porous filter and the face mask. The air flow system includes an enclosed container and a blower housed within the enclosed container. The air flow system is configured to generate a flow of air such that ambient air passes through the porous filter to the face mask. The decontamination device is configured to removably receive the porous filter of the at least one respirator. The decontamination device includes an oxidant generator configured to produce at least one oxidant. At least one contaminant in the flow of air is adsorbed by the porous filter, and the filtration material catalyzes an oxidation reaction between the oxidant and the contaminant to promote decomposition of the contaminant on the porous filter.

According to another aspect, provided is an air purification system including at least one respirator and a decontamination device. The at least one respirator includes a face mask, a mechanical filter, and an air flow system in fluid communication with the mechanical filter and the face mask. The air flow system includes an enclosed container and a blower housed within the enclosed container. The air flow system is configured to generate a flow of air such that ambient air passes through the mechanical filter to the face mask. The decontamination device is configured to removably receive the mechanical filter of the at least one respirator. The decontamination device includes an oxidant generator configured to produce at least one oxidant. At least one pathogen in the flow of air is captured by the mechanical filter, and the oxidant promotes disinfection of the pathogen on the mechanical filter.

According to another aspect, provided is an air purification system including at least one respirator and a decontamination device. The at least one respirator includes a face mask, a removable filter case, and an air flow system in fluid communication with the removable filter case and the face mask. The face mask includes a mask inlet valve and a mask outlet valve. The removable filter case includes at least one filter and a rechargeable battery. The at least one filter is a mechanical filter or a porous filter comprising a filtration material. The air flow system includes an enclosed container, an air inlet and an air outlet disposed on the enclosed container, a chamber in the enclosed container to accommodate the removable filter case, a blower housed within the enclosed container, and a tube. The blower is configured to generate a flow of air such that ambient air passes through the removable filter case through the filter to the air outlet and to the face mask. The tube connects the air outlet of the enclosed container and the face mask. The decontamination device is configured to removably receive the mechanical filter of the at least one respirator. The decontamination device includes at least one filter cage configured to receive the removable filter case of the at least one respirator, a blower configured to direct an airstream towards the removable filter case, an oxidant generator configured to produce at least one oxidant, and a charging unit configured to provide electrical current to recharge the battery. At least one contaminant in the flow of air is adsorbed by the porous filter. The filtration material catalyzes an oxidation reaction between the oxidant and the contaminant to promote decomposition of the contaminant on the porous filter. The oxidant oxidizes the contaminant to promote decomposition of the contaminant in the removable filter case.

In some embodiments, the filtration material includes zeolite having a pore size in the range of 2 Angstroms to 20 Angstroms.

In some embodiments, the respirator further comprises a mechanical filter positioned before the porous filter along the direction of the flow of air. In some embodiments, the mechanical filter is a high-efficiency particulate air (HEPA) filter.

In some embodiments, the oxidant generator is an ozone generator and the oxidant is ozone.

In some embodiments, the respirator further comprises a battery that provides power to operate the air flow system and the oxidant generator.

In some embodiments, the porous filter and the battery are contained in a removable filter case, and the enclosed container further comprises a chamber to receive the removable filter case.

In some embodiments, the decontamination device is further configured to provide electrical current to recharge the battery.

In some embodiments, the decontamination device further comprises a blower configured to direct an airstream towards the porous filter.

In some embodiments, the air flow system further comprises a control unit configured to perform one or more of the following: (a) switch on or switch off the air flow system; (b) adjust a speed of the flow of air; (c) detect a back pressure in the air flow system; (d) control a rate of oxidant production by the oxidant generator; and (e) control and monitor an operation of the respirator.

According to another aspect, provided is a method of providing purified air to a user by an air flow system in fluid communication with a porous filter comprising a filtration material and a face mask. The method comprises the steps of: (i) generating a flow of air by the air flow system through the porous filter to the face mask, wherein the porous filter adsorbs at least one contaminant in the flow of air to produce the purified air; and (ii) producing at least one oxidant by an oxidant generator. The filtration material is capable of catalyzing an oxidation reaction between the oxidant and the contaminant to promote decomposition of the contaminant on the porous filter.

According to another aspect, provided is a method of regenerating a porous filter comprising a filtration material using the air purification system as described, comprising the steps of (i) generating a flow of air by the air flow system of the respirator through the porous filter such that the filtration material adsorbs at least one contaminant in the flow of air; (ii) producing at least one oxidant by an oxidant generator to decompose the at least one contaminant on the porous filter; and (iii) catalyzing an oxidation reaction between the oxidant and the contaminant by the filtration material to promote decomposition of the contaminant on the porous filter thereby regenerating the porous filter.

In some embodiments, the oxidation reaction is done in a separate decontamination device. Accordingly in some embodiments, the method further comprises the step of removing the porous filter comprising the filtration material from the respirator and inserting it into the decontamination device.

According to another aspect, provided is a method of disinfecting a mechanical filter using the air purification system as described, comprising the steps of (i) inserting the mechanical filter into a decontamination device comprising an oxidant generator; and (ii) producing at least one oxidant by the oxidant generator of the decontamination device to disinfect at least one pathogen on the mechanical filter, thereby ensuring that the mechanical filter is safe to dispose.

There are many advantages to the various embodiments of the present disclosure. For instance, some embodiments provide a respirator with a built-in oxidant generator that is capable of decontaminating and regenerating the porous filter so that the respirator can be used for a longer period of time without filter replacement. This will enable a user of the respirator to be protected when working for a long time in an environment or an indoor space where harmful contaminants are present.

In some embodiments, the filter is removable from the respirator and is reusable after it is regenerated using the decontamination device. In some embodiments, the filter and the battery is contained in a single removable filter case, and the decontamination device is capable of regenerating the filter and recharge the battery at the same time. As a result, it is easy and convenient for a user to make the necessary replacement with minimal steps, i.e. by removing the used filter case from the respirator and inserting the recharged and regenerated filter case into the respirator. It also provides a less expensive, safer, and more environmental friendly maintenance and operating procedure.

In some embodiments, the decontamination device is capable of disinfecting pathogens captured by the mechanical filter, thereby offering a low cost solution for safe disposal of the used filter.

DETAILED DESCRIPTION

Figure 1:
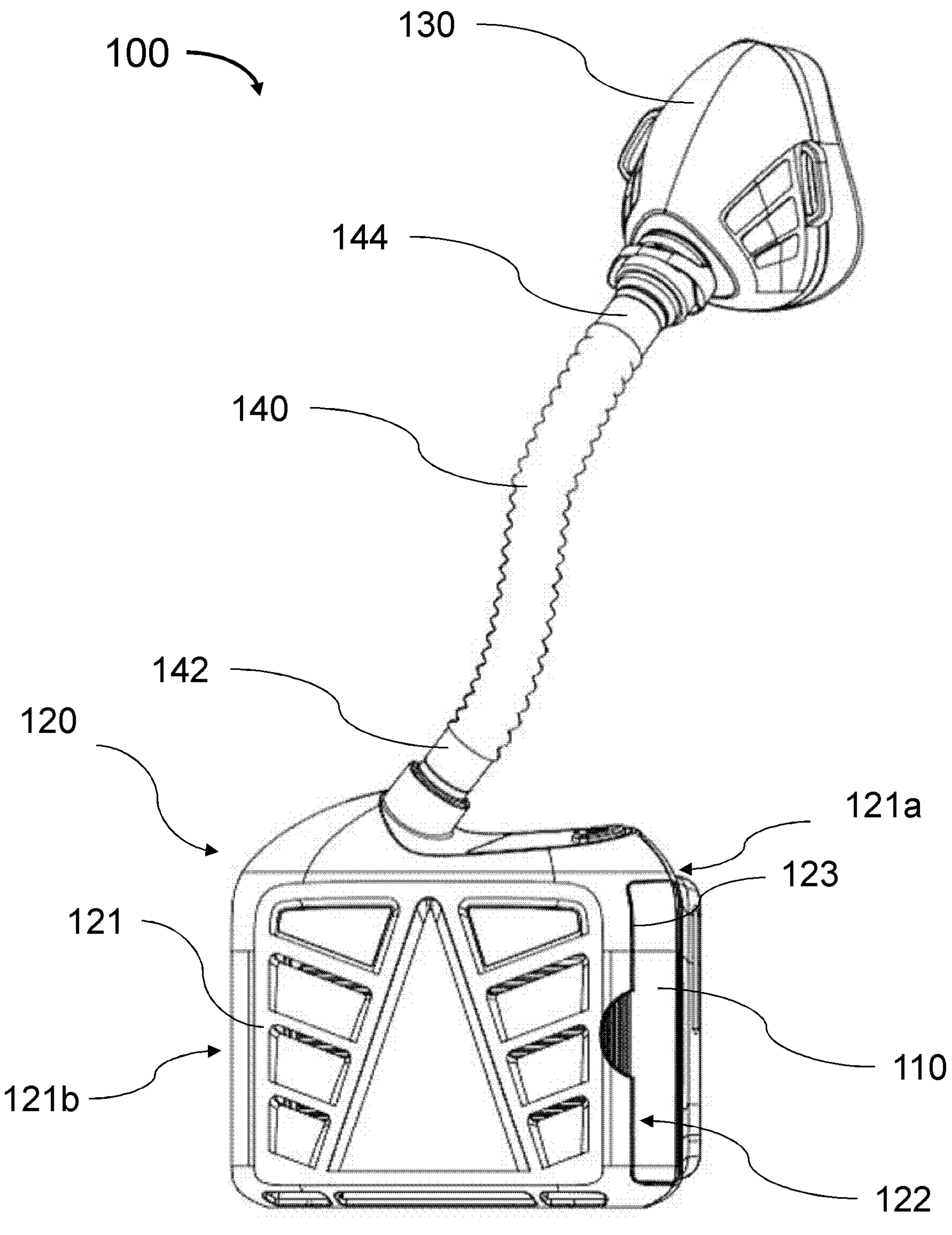
FIG. 1 is a perspective view of a respirator in accordance with an example embodiment.

As used herein and in the claims, "comprising" means including the following elements but not excluding others.

As used herein and in the claims, "fluid communication" refers to configuration of two or more components such that a fluid (e.g. a gas) is capable of moving from one component to another component that are connected directly or indirectly with each other. In some embodiments, fluid communications refers to the ability of fluid to move by pressure differences from one component that is connected to another component.

As used herein and in the claims, "enclosed" refers to the state of a structure that is at least partially airtight with the exception of one or more openings to allow for air entrance or exit.

As used herein and in the claims, "contaminant" refers to certain potentially harmful or irritating elements of air. Examples of contaminant include but not limited to CO, smoke, aerosols, TVOC's (Total Volatile Organic Compounds), specific VOC's of interest, formaldehyde, alkanol, methylene chloride, toluene, benzene, aliphatic hydrocarbon, NO, NOX, SOX, SO2, hydrogen sulfide, chlorine, nitrous oxide, methane, hydrocarbons, ammonia, refrigerant gases and other toxic gases.

As used herein and in the claims, "pathogen" refers to any organism or molecule that is associated with or causes a disease or condition to a subject. Examples of pathogen include but not limited to viruses, fungi, bacteria, parasites, archaea, *mycoplasma*, parasitic organisms and other infectious organisms or molecules therefrom. In some embodiments, pathogen include any organism or molecule that have a negative impact on human health, for example agents that cause allergic reactions, physical pain, itching, obesity, reduced metabolic rate, metabolic syndrome, diabetes, cardiovascular disease, hyperlipidemia, neurodegenerative diseases, cognitive disorders, mood disorders, stress and anxiety disorders.

As used herein and in the claims, "porous filter" refers to a filter comprising filtration material. The total porosity and the pore size can be varied according to the filtering material. In some embodiments, the filtration material is also capable of catalyzing an oxidation reaction between an oxidant and the contaminant to promote decomposition of the contaminant on the porous filter.

As used herein and in the claims, "mechanical filter" refers to a filter that prevents the passage of particles by having holes that are smaller than the particles in the filter. Examples of mechanical filter includes high efficiency particulate air (HEPA) filter and ultra-low penetration air (ULPA) filters. In some embodiments, the mechanical filter is capable of preventing the passage of particles and pathogens.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "front", "back", "top", "bottom", "left", "right" or the like, these words are used to describe the relative position between the elements for convenience of description, and thus will not limit the example embodiments.

In some embodiments, provided is a respirator including a face mask, a porous filter comprising a filtration material, an air flow system in fluid communication with the porous filter and the face mask, and an oxidant generator configured to produce at least one oxidant. The air flow system includes an enclosed container and a blower housed within the enclosed container. The air flow system is configured to generate a flow of air such that ambient air passes through the porous filter to the face mask. At least one contaminant in the flow of air is adsorbed by the porous filter, and the filtration material catalyzes an oxidation reaction between the oxidant and the contaminant to promote decomposition of the contaminant on the porous filter.

In some embodiments, the oxidant generator is positioned before the porous filter along the direction of the flow of air.

In some embodiments, the filtration material has a pore size that permits adsorption of the contaminant and the oxidant.

In some embodiments, the filtration material comprises zeolite having a pore size in the range of 2 Angstroms to 20 Angstroms.

In some embodiments, the respirator further comprises a mechanical filter positioned before the porous filter along the direction of the flow of air.

In some embodiments, the mechanical filter is a high-efficiency particulate air (HEPA) filter.

In some embodiments, the oxidant generator is an ozone generator and the oxidant is ozone.

In some embodiments, the air flow system further comprises a tube connecting the enclosed container to the face mask, such that the flow of air passes through the tube.

In some embodiments, the face mask comprises a mask inlet valve and a mask outlet valve, wherein the tube connects the enclosed container to the face mask through the mask inlet valve, and the mask inlet valve is configured for a one-way flow of air into the face mask.

In some embodiments, the air flow system further comprises a second tube connecting the face mask to the enclosed container, and the mask outlet valve of the face mask is connected to the second tube and configured for a one-way flow of air out of the face mask.

In some embodiments, the respirator further comprises a battery that provides power to operate the air flow system and the oxidant generator.

In some embodiments, the porous filter and the battery are contained in a removable filter case, and the enclosed container further comprises a chamber to receive the removable filter case.

In some embodiments, the air flow system further comprises a control unit configured to perform one or more of the following:

a) switch on or switch off the air flow system;

b) adjust a speed of the flow of air;

c) detect a back pressure in the air flow system;

d) control a rate of oxidant production by the oxidant generator; and e) control and monitor an operation of the respirator.

In some embodiments, provided is an air purification system including at least one respirator and a decontamination device. The at least one respirator includes a face mask, a porous filter comprising a filtration material, and an air flow system in fluid communication with the porous filter and the face mask. The air flow system includes an enclosed container and a blower housed within the enclosed container. The air flow system is configured to generate a flow of air such that ambient air passes through the porous filter to the face mask. The decontamination device is configured to removably receive the porous filter of the at least one respirator. The decontamination device includes an oxidant generator configured to produce at least one oxidant. At least one contaminant in the flow of air is adsorbed by the porous filter, and the filtration material catalyzes an oxidation reaction between the oxidant and the contaminant to promote decomposition of the contaminant on the porous filter.

In some embodiments, the filtration material has a pore size that permits adsorption of both the contaminant and the oxidants.

In some embodiments, the filtration material comprises zeolite having a pore size in the range of 2 Angstroms to 20 Angstroms.

In some embodiments, the respirator further comprises a mechanical filter positioned before the porous filter along the direction of the flow of air.

In some embodiments, the mechanical filter is a high-efficiency particulate air (HEPA) filter.

In some embodiments, the respirator further comprises a built-in oxidant generator positioned before the porous filter along the direction of the flow of air.

In some embodiments, the respirator further comprises a battery that provides power to operate the air flow system.

In some embodiments, the respirator further comprises a removable filter case that houses the porous filter and the battery, and the enclosed container comprises a chamber to accommodate the removable filter case.

In some embodiments, the decontamination device is further configured to provide electrical current to recharge the battery.

In some embodiments, the decontamination device further comprises a blower configured to direct an airstream towards the porous filter.

In some embodiments, provided is an air purification system including at least one respirator and a decontamination device. The at least one respirator includes a face mask, a mechanical filter, and an air flow system in fluid communication with the mechanical filter and the face mask. The air flow system includes an enclosed container and a blower housed within the enclosed container. The air flow system is configured to generate a flow of air such that ambient air passes through the mechanical filter to the face mask. The decontamination device is configured to removably receive the mechanical filter of the at least one respirator. The decontamination device includes an oxidant generator configured to produce at least one oxidant. At least one pathogen in the flow of air is captured by the mechanical filter, and the oxidant promotes disinfection of the pathogen on the mechanical filter.

In some embodiments, the mechanical filter is a high-efficiency particulate air (HEPA) filter.

In some embodiments, the respirator further comprises a battery that provides power to operate the air flow system.

In some embodiments, the respirator further comprises a removable filter case to house the mechanical filter and the battery, and the enclosed container further comprises enclosure chamber to receive the removable filter case.

In some embodiments, the decontamination device is further configured to provide electrical current to recharge the battery.

In some embodiments, the oxidant generator is an ozone generator and the oxidant is ozone.

In some embodiments, the air flow system further comprises a tube connecting the enclosed container to the face mask, such that the flow of air passes through the tube.

In some embodiments, the face mask comprises a mask inlet valve and a mask outlet valve, wherein the tube connects the enclosed container to the face mask through the mask inlet valve, and the mask inlet valve is configured for a one-way flow of air into the face mask.

In some embodiments, the air flow system further comprises a second tube connecting the face mask to the enclosed container, and the mask outlet valve of the face mask is connected to the second tube and configured for a one-way flow of air out of the face mask.

In some embodiments, provided is an air purification system including at least one respirator and a decontamination device. The at least one respirator includes a face mask, a removable filter case, and an air flow system in fluid communication with the removable filter case and the face mask. The face mask includes a mask inlet valve and a mask outlet valve. The removable filter case includes at least one filter and a rechargeable battery. The at least one filter is a mechanical filter or a porous filter comprising a filtration material. The air flow system includes an enclosed container, an air inlet and an air outlet disposed on the enclosed container, a chamber in the enclosed container to accommodate the removable filter case, a blower housed within the enclosed container, and a tube. The blower is configured to generate a flow of air such that ambient air passes through the removable filter case through the filter to the air outlet and to the face mask. The tube connects the air outlet of the enclosed container and the face mask. The decontamination device is configured to removably receive the mechanical filter of the at least one respirator. The decontamination device includes at least one filter cage configured to receive the removable filter case of the at least one respirator, a blower configured to direct an airstream towards the removable filter case, an oxidant generator configured to produce at least one oxidant, and a charging unit configured to provide electrical current to recharge the battery. At least one contaminant in the flow of air is adsorbed by the porous filter. The filtration material catalyzes an oxidation reaction between the oxidant and the contaminant to promote decomposition of the contaminant on the porous filter. The oxidant oxidizes the contaminant to promote decomposition of the contaminant in the removable filter case.

In some embodiments, the respirator further comprises a built-in oxidant generator positioned before the removable filter case along the direction of the flow of air.

In some embodiments, the face mask comprises a mask inlet valve and a mask outlet valve, wherein the mask inlet valve is connected to the tube and configured for a one-way flow of air into the face mask.

In some embodiments, the air flow system further comprises a second tube connecting the face mask to the enclosed container to enable the flow of air from the face mask to the enclosed container, and the mask outlet valve of the face mask is connected with the second tube and configured for a one-way flow of air into the enclosed container.

In some embodiments, the at least one filter cage is configured as a plurality of modular filter cartridges that are removably connected with and fluidly communicated with each other, wherein each modular filter cartridge is configured to receive one filter cage.

In some embodiments, the air flow system further comprises a control unit configured to perform one or more of the following: (a) switch on or switch off the air flow system; (b) adjust a speed of the flow of air; (c) detect a back pressure in the air flow system; (d) control a rate of oxidant production by the oxidant generator; and (e) control and monitor an operation of the respirator.

In some embodiments, provided is a method of providing purified air to a user by an air flow system in fluid communication with a porous filter comprising a filtration material and a face mask. The method comprises the steps of: (i) generating a flow of air by the air flow system through the porous filter to the face mask, wherein the porous filter adsorbs at least one contaminant in the flow of air to produce the purified air; and (ii) producing at least one oxidant by an oxidant generator. The filtration material is capable of catalyzing an oxidation reaction between the oxidant and the contaminant to promote decomposition of the contaminant on the porous filter.

In some embodiments, provided is a method of regenerating a porous filter comprising a filtration material using the air purification system as described, comprising the steps of (i) generating a flow of air by the air flow system of the respirator through the porous filter such that the filtration material adsorbs at least one contaminant in the flow of air; (ii) producing at least one oxidant by an oxidant generator to decompose the at least one contaminant on the porous filter; and (iii) catalyzing an oxidation reaction between the oxidant and the contaminant by the filtration material to promote decomposition of the contaminant on the porous filter thereby regenerating the porous filter.

In some embodiments, provided is a method of disinfecting a mechanical filter using the air purification system as described, comprising the steps of (i) inserting the mechanical filter into a decontamination device comprising an oxidant generator; and (ii) producing at least one oxidant by the oxidant generator of the decontamination device to disinfect at least one pathogen on the mechanical filter, thereby ensuring that the mechanical filter is safe to dispose.

In the following description, same numberings are employed to illustrate the same components of different figures.

Provided herein are examples that describe in more detail certain embodiments of the present disclosure. The examples provided herein are merely for illustrative purposes and are not meant to limit the scope of the invention in any way. All references given below and elsewhere in the present application are hereby included by reference.

Example 1

Respirator

Referring now to FIG. 1, which shows an example embodiment of a respirator 100. The respirator 100 includes a face mask 130, an air flow system 120 and a removable filter case 110 (partially shown). The air flow system 120 is in fluid communication with the removable filter case 110 and the face mask 130. The air flow system 120 includes an enclosed container. In this embodiment, the enclosed container is container 121 with a generally rounded rectangular shape. The container 121 has a receiving hole 123 cut on a side surface of the container 121 and forms an open end 121*a*. The opposing side surface is a closed end 121*b*. For ease of description, the closed end 121*b* is called left side and open end 121*a* is called right side. The container 121 defines a chamber 122 configured to receive the removable filter case 110 through the receiving hole 123, such that the removable filter case 110 is operably coupled to the air flow system 120 when it is inserted into the chamber 122. The chamber 122 is shaped and sized to match with the removable filter case 110 to ensure a generally air-tight connection between them when it is inserted. The air flow system 120 further includes a tube 140 connecting the container 121 to the face mask 130 in fluid communication to enable a flow of air from the container 121 to the face mask 130. The tube 140 has a first end 142 adapted to be connected to the container 121 and a second end 144 adapted to be connected to the face mask 130. Each of the first end 142 and the second end 144 is fitted with a connecting ring to secure the connection with its counterpart. Each of these components will be described in greater detail below.

In some other embodiments, the respirator 100 may only include a porous filter and/or a mechanical filter without a removable filter case 110. The porous filter and the mechanical filters will be described in greater detail below. In some embodiments, the respirator 100 may be carried by a user around his waist via a belt (not shown) attached to the container 121 or by any other suitable means.

Figure 2A:
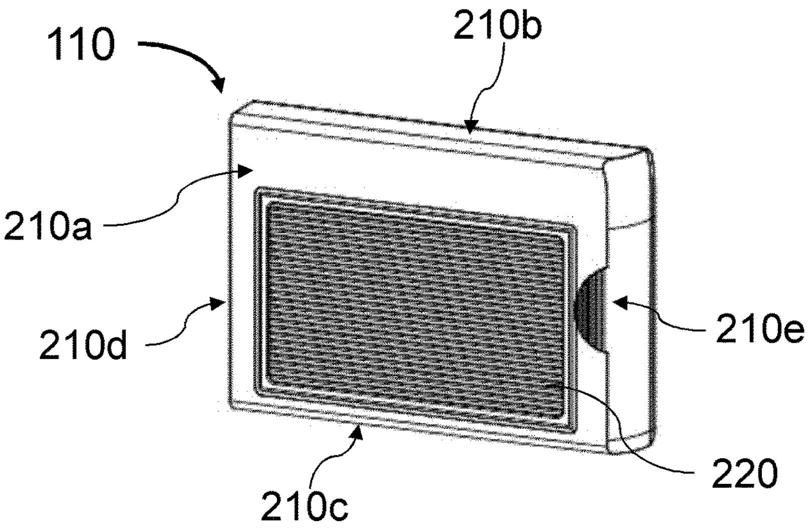
FIG. 2A is a perspective view of a removable filter case in accordance with an example embodiment.
Figure 2B:
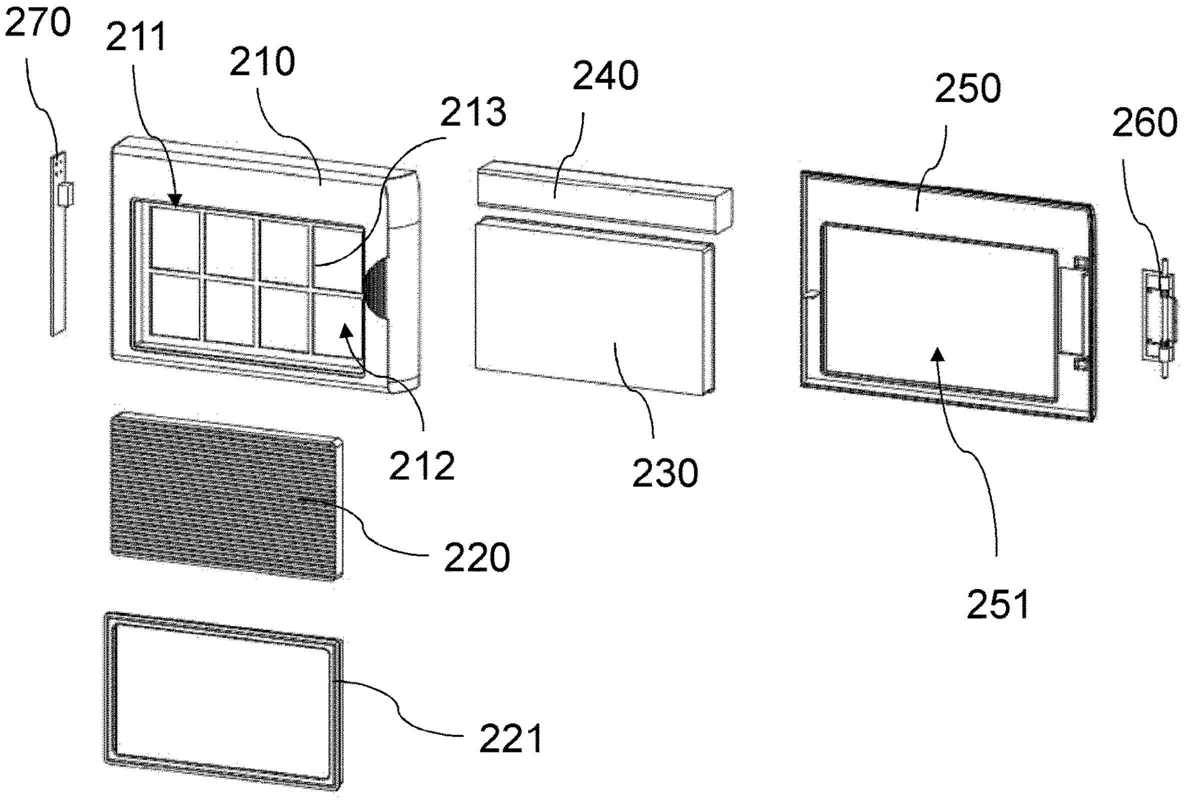
FIG. 2B is a schematic exploded view of a removable filter case according to the same example embodiment as illustrated in FIG. 2A.

Referring now to FIGS. 2A and 2B, which show the removable filter case 110 of FIG. 1. The removable filter case 110 has a horizontal rectangular shape with rounded corners and includes a front case 210 and a back case 250 joining together to form the removable filter case 110. For ease of description, the side closer to the front case 210 is called the front side and the side closer to the back case 250 is called the back side. In this embodiment, the front case 210 forms a front surface 210*a*, a back surface (not shown), a top surface 210*b*, a bottom surface 210*c*, a left side surface 210*d* and an opposing right side surface 210*e* of the removable filter case 110. A snap lock 260 is disposed on the right side of the back case 250 to secure the position of the removable filter case 110 when it is inserted into the chamber 122 of the container 121 shown in FIG. 1.

In this embodiment, the removable filter case 110 has a cavity 212 in a horizontal rectangular shape. A front case opening 211 is provided on the front case 210 and a back case opening 251 is provided on the back case 250 to permit air to pass through the cavity 212. The removable filter case 110 includes two filters 220 and 230 fitted within the cavity 212. A divider 213 with eight holes is disposed on the front case 210 and divides the cavity 212 into front half and back half to accommodate filters 220 and 230 respectively. this embodiment, filters 220 and 230 are shaped and sized to match the front half and the back half of the cavity 212 respectively to ensure that the filters are tightly fit within the cavity 212 without any air leakage. Filter 220 is fitted into the front half of the cavity 212 via the front case opening 211, and filter 230 is fitted into the back half of the cavity 212 via the back case opening 251. When fitted within the cavity 212, filters 220 and 230 are arranged juxtapose to each other with filter 220 at the front and filter 230 at the back. A frame 221 having a frame opening is provided in front of the filter 220 to secure the position of the filter 220 within the cavity 212 when it is fitted therein. In some embodiments, the filter 220 and 230 can be removed from the removable filter case 110 and be replaced.

In this embodiment, the removable filter case 110 also includes a battery 240 housed within the top part of the removable filter case 110. The battery 240 has a bar shape and positioned horizontally on top of the filters 220 and 230. The removable filter case 110 includes an electrical connector 270 attached to the side surface 210*d* of the removable filter case 110. The electrical connector 270 is in electrical connection with the battery 240. The battery 240 is configured to provide power to operate the air flow system 120 (not shown in this figure but will be shown in FIG. 3). In some embodiments, the battery 240 is rechargeable and/or replaceable. In some embodiments, the battery 240 can be made of lithium ion, lithium polymer or other high capacity battery. In some embodiments, the battery 240 has a capacity of 3200 mAh. In some embodiments, the battery 240 supports at least around 4 hours of operation when it is fully charged.

In this embodiment, filter 220 is a mechanical filter and filter 230 is a porous filter. In some embodiments, filter 220 and 230 are both mechanical filters. In some embodiments, filter 220 and 230 are both porous filters. In some embodiments, the removable filter case 110 includes only one filter 220 or 230.

In some embodiments, the mechanical filter is a high efficiency particulate air (HEPA) filter. The mechanical filter is capable of capturing particles and pathogens in the air.

In some embodiments, the porous filter includes at least one filtration material. The filtration material is capable of adsorbing at least one contaminant in the air. The filtration material is also capable of catalyzing an oxidation reaction between at least one oxidant and the contaminant to promote decomposition of the contaminant on the porous filter. The filtration material secures the adsorbed contaminant and oxidant into a confined space, and provides active sites in which the oxidant can more effectively react with the contaminant. In some embodiment, the filtration material has a pore size that permits adsorption of both the contaminant and the oxidant such that the oxidation reaction can be carried out. In some embodiments, the type and pore size of the filtration material used may be determined after evaluation tests are performed to establish which contaminant is present in a specific space.

In some embodiments, the filtration material includes at least one molecular sieve. In some embodiments, the filtration material includes zeolite having a pore size in the range of 2 Angstroms to 20 Angstroms. In some embodiments, the zeolite is a hydrophilic zeolite, which are used for an environment in which polar contaminants such as formaldehyde, alkanol, methylene chloride are dominant. In some embodiments, the zeolite is a hydrophobic zeolite, which are used for an environment in which non-polar contaminants such as toluene, benzene, aliphatic hydrocarbon are dominant.

In some embodiments, the filtration material includes crystalline porous materials with pore sizes complementary to zeolite that are effective in trapping contaminant gas molecules. The crystalline porous materials may be metal oxide frameworks consisting of transition metals. The transition metals incorporated in the metal oxide frameworks will act as catalysts for oxidation of the contaminants.

Figure 3:
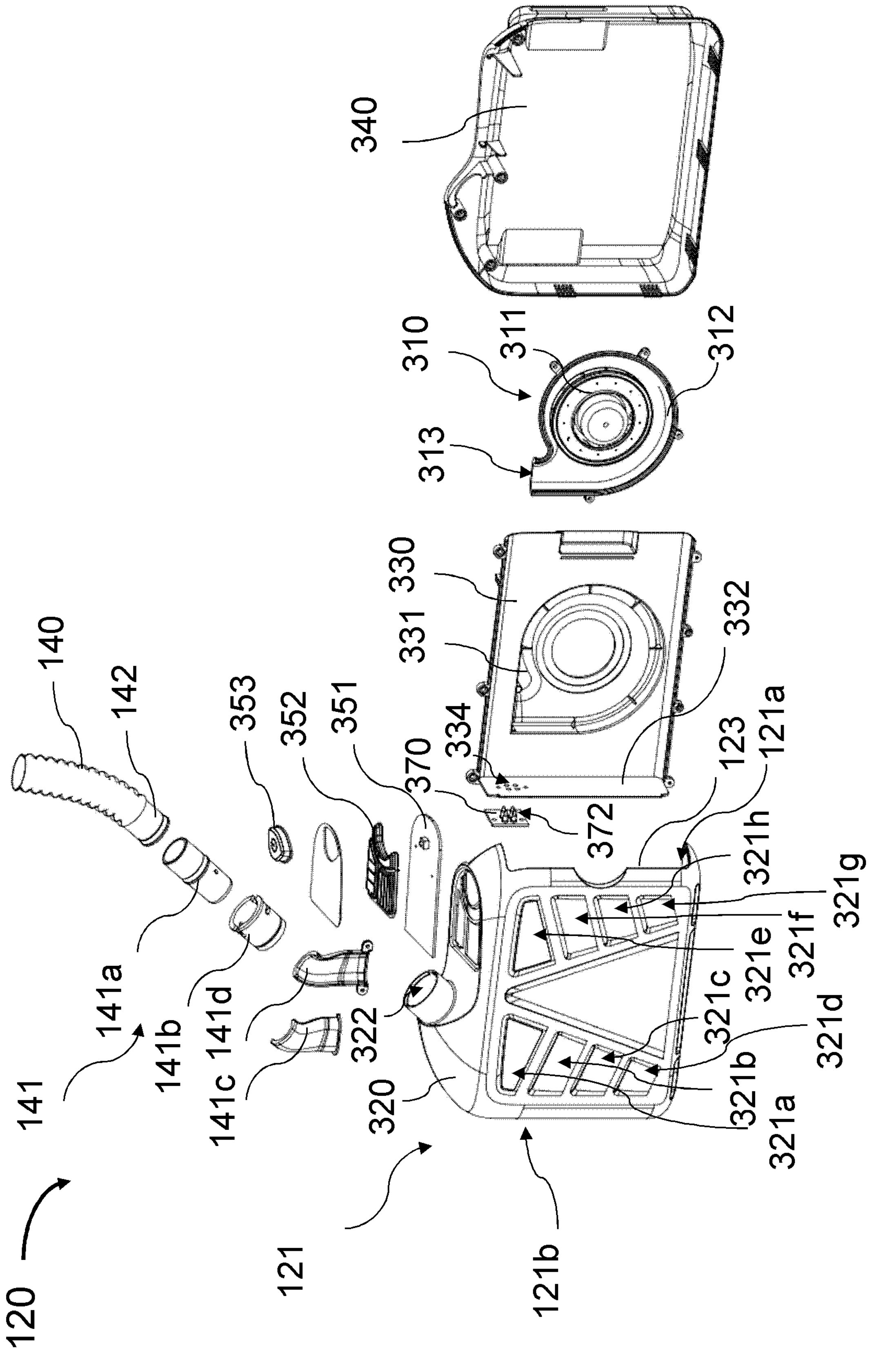
FIG. 3 is a schematic exploded view of an air flow system in accordance with an example embodiment.

Referring now to FIG. 3, which shows an exploded view of the container 121 and a portion of the tube 140 of the air flow system 120 as illustrated in FIG. 1. The container 121 includes a front cover 320 and a back cover 340 assembled together to form an enclosure within the container 121. In this example embodiment, the container 121 further includes a middle panel 330 positioned between the front cover 320 and the back cover 340.

Referring now to FIGS. 1, 2A and 3, the front cover 320 and the middle panel 330, when fitted together, defines a chamber 122 which is configured to accommodate the removable filter case 110.

The air flow system 120 may include at least one air inlet and at least one air outlet disposed on the container 121. In this embodiment, the front cover 320 of the container 121 defines eight holes as the air inlets 321*a-h*. Referring now to FIGS. 1, 2A and 3, when the removable filter case 110 is inserted into the chamber 122 of the container 121, the front surface 210*a* of the removable filter case 110 is facing the air inlets 321*a-h* of the front cover 320 such that the air from air inlet can pass through filter case. The air inlets 321*a-h* allow ambient air to enter the container 121 into the chamber 122 which the removable filter case 110 is situated. The air outlet 322 is disposed on the top of the front cover 320. The first end 142 of the tube 140 is connected to the container 121 via the air outlet 322 to allow air to flow out of the container 121. In some embodiments, the air flow system 120 includes a connector assembly 141 formed by four connector parts 141*a* 141*b*, 141*c* and 141*d* (FIG. 3). The connector assembly 141 is adapted to provide an air-tight connection between the first end 142 of the tube 140 and the air outlet 322 on the container 121.

The air flow system 120 includes a blower assembly 310 housed in the container 121. In this embodiment, a socket 331 extended backwards towards the back cover 340 and shaped to fit the blower assembly 310 is provided in the middle panel 330 for the blower assembly 310 to be housed therein. The middle panel 330 and the back cover 340, when fitted together, form a space with a sufficient thickness to accommodate at least part of the blower assembly 310.

The blower assembly 310 includes a blower 311 having a circular perimeter and a blower frame 312 shaped to surround the circular perimeter of the blower 311 and has an opening 313 connected to the air outlet 322. The blower 311 is configured to generate a flow of air such that ambient air enters the container 121 through the air inlets, flows into the blower 311, exits the container 121 through the opening 313 connected to the air outlet 322, and passes through the tube 140 to enter the face mask (not shown).

Referring now to FIGS. 1, 2A, 2B and 3, when the removable filter case 110 is inserted into the chamber 122 of the container 121, the removable filter case 110 is positioned directly in front of the blower assembly 310, with the back case opening 251 facing the front of the blower assembly 310. As a result, the flow of air generated by the blower 311 passes through the filter housed in the removable filter case 110 before flows through the blower 311 and to the opening 313 connected to the air outlet 322.

In some embodiments, the blower 311 may also be fitted in front of the chamber 122, such that when the removable filter case 110 is inserted into the chamber 122, the blower 311 is positioned before the removable filter case 110 along the direction of the flow of air. As a result, the flow of air will first flow through the blower 311 and then passes through the filter housed in the removable filter case 110 and to the air outlet 322.

In this embodiment, the middle panel 330 has a side plate 332 positioned on the left end of the middle panel 330 and extended substantially perpendicular to the middle panel 330 towards the front, forming an L-shaped structure with the middle panel 330 (FIG. 3). Four pin holes 334 are disposed on the side plate 332. An electrical connection port 370 with four electrical contact pins 372 is attached to left side of the side plate 332 and secured by two screws. The four electrical contact pins 372 pass through the four pin holes 334 and protrude out from the right side of the side plate 332. Referring now to FIGS. 2B and 3, when the removable filter case 110 is inserted into the container 121, the electrical connection port 370 is situated juxtapose to the electrical connector 270. This configuration allows the electrical contact pins 372 to be electrically connected with the battery 240 via the electrical connector 270 to provide power to operate the air flow system 120.

In some embodiments, the air flow system 120 includes an oxidant generator (not shown in this Figure) configured to produce at least one oxidant. In some embodiments, the oxidant generator is positioned before the removable filter case 110 (not shown) along the direction of the flow of air. In some embodiments, the oxidant generator is mounted on an inner surface of the front cover 320. In some embodiments, the oxidant generator is an ozone generator and the oxidant is ozone. In some other embodiments, the oxidant generator is a hydroxyl radical generator and the oxidant is one or more hydroxyl radicals. In some other embodiments, the oxidant generator is an ion generator and the oxidant is one or more ions. In some other embodiments, the oxidant is ozone, one or more hydroxyl radicals, ions or a combination thereof.

In this embodiment, the air flow system 120 further comprises a control unit 351 disposed on the top of the front cover 320. The control unit 351 is electrically connected with the blower 311 of the air flow system 120 and the battery 240 (not shown). In some embodiments, the control unit 351 is electrically connected with the oxidant generator. The control unit 351 is configured to perform one or more of the following: a. switch on or switch off the air flow system 120; b. adjust a speed of the flow of air; c. detect a back pressure in the air flow system 120 and adjust the speed of the flow of air accordingly; d. control a rate of oxidant production by the oxidant generator; and e. control and monitor an operation of the air flow system 120. In some embodiments, the blower 311 is configured to generate at least one predetermined speed of the flow of air, and the predetermined speed can be selected/adjusted by a user through the control unit 351. In some embodiments, the control unit 351 may include one or more sensors to detect a back pressure in the air flow system 120. The control unit 351 may automatically adjust the speed of the flow of air based on the back pressure to maintain the stability of air flow system 120. In some embodiments, the control unit 351 may include one or more oxidant sensor to monitor the level of oxidant in the air flow system 120, particularly after the flow of air passes through the filters. If the oxidant level exceeds a certain amount, the control unit 351 will instruct the oxidant generator to stop generating the oxidant to ensure that no or minimal level of oxidant remains in the flow of air after it passes through the filters. This will ensure that the flow of air that reaches the face mask does not contain an excessive level of oxidant that is hazardous to human health.

In this embodiment, the air flow system 120 further includes a switch 353 disposed on the top of the front cover 320 of the container 121. The switch 353 is electrically connected to the control unit 351 and configured to switch on or switch off the air flow system 120. In some embodiments, the switch 353 is further configured to select the predetermined speed of the flow of air.

In this embodiment, the air flow system 120 further comprises a display unit 352 disposed on the top of the front cover 320 of the container 121 and attached on top of the control unit 351. The display unit 352 is in electrical connection with the control unit 351 and configured to display information of the status of respirator 100, such as the remaining power of the battery 240, speed of the blower 311, rate of the flow of air etc. In some embodiments, the display unit 450 can be either a liquid-crystal display (LCD), Light-Emitting Diode (LED) or other kind of display.

Figure 4A:
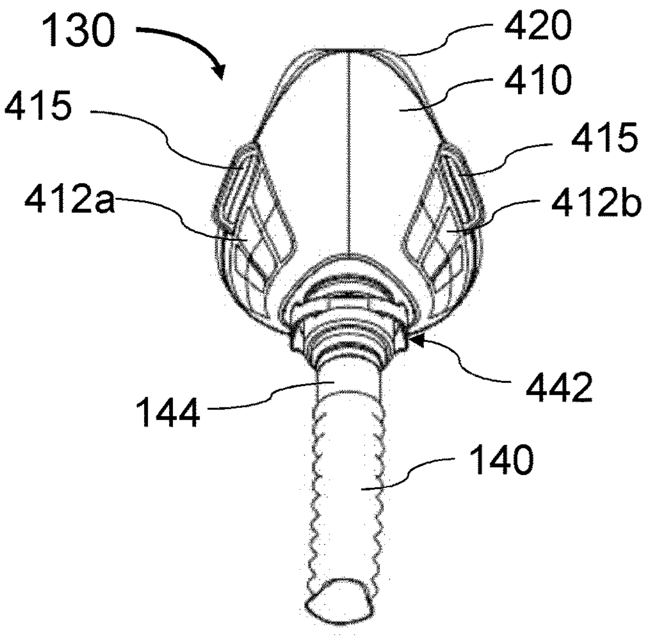
FIG. 4A is a schematic a top view of a face mask in accordance with an example embodiment.
Figure 4B:
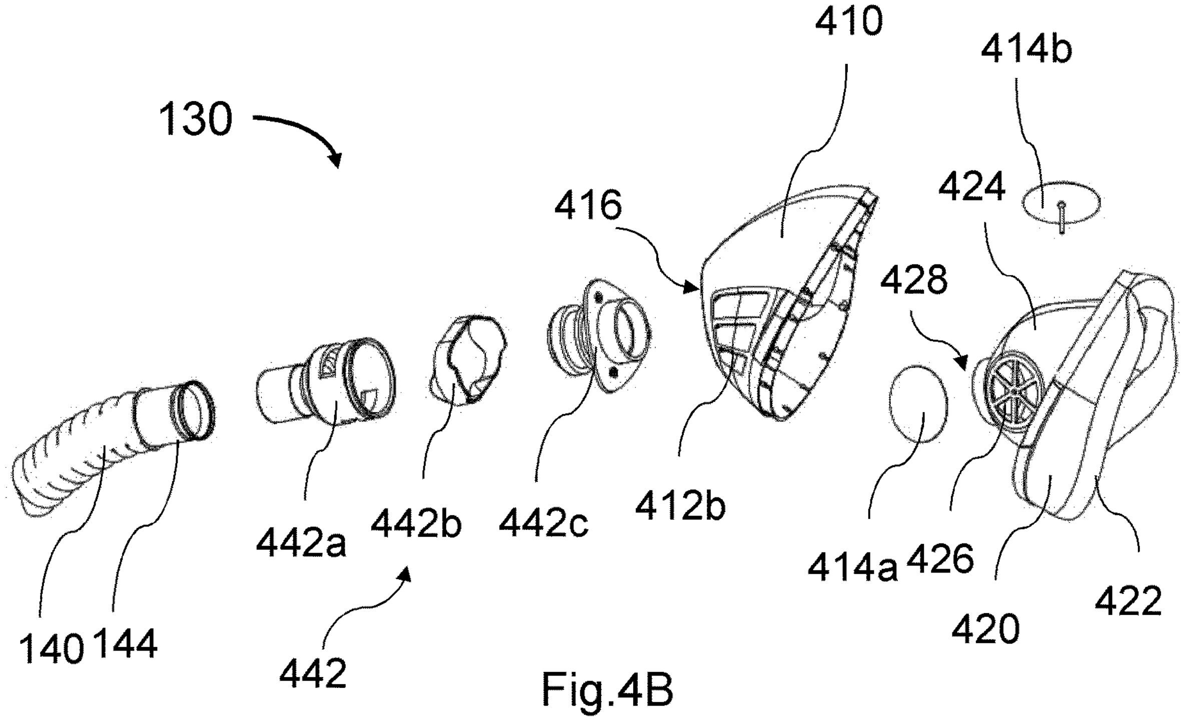
FIG. 4B is schematic exploded view of a face mask according to the same example embodiment as illustrated in FIG. 4A.

FIGS. 4A and 4B show the face mask 130 and a portion of tube 140 connecting with the face mask 130 as shown in FIG. 1. The face mask 130 includes a mask shell 410 and a mask body 420. The mask body 420 is adapted to engage a user's face, and the mask shell 410 is attached to the mask body 420 to provide support for the mask body 420.

Referring to FIG. 4B, the mask body 420 has a nasal portion 424 and a face-contacting portion 422. The face-contacting portion 422 is shaped to provide a generally sealed structure to cover at least the nose and preferably also the mouth of the user. In some embodiments, the nasal portion 424 and the face-contacting portion 422 are integrally formed as one piece. In some other embodiments, the nasal portion 424 and the face-contacting portion 422 are fixedly connected with each other. In some other embodiments, the nasal portion 424 and the face-contacting portion 422 are individual parts that can be separated from, or connected with each other. In some embodiment, the mask body 420 is made of silicone. In this example embodiment, the face mask 130 includes an inhalation hole 428 provided on the center of the nasal portion 424 of the mask body 420. The inhalation hole 428 is removably engaged with the second end 144 of tube 140 through a connector assembly 442. In this example embodiment, the connector assembly 442 is formed by a number of connector parts 442*a*, 442*b* and 442*c*. The connector assembly 442 is adapted to provide an air-tight connection between the second end 144 of the tube 140 and the inhalation hole 428 of the mask body 420. In this embodiment, the mask body 420 includes two exhalation holes provided on each lateral side of the nasal portion 424. Only one exhalation hole 426 is shown here but it is understood that another exhalation hole is present on the opposite lateral side of the nasal portion 424. Exhalation hole 426 is operably coupled to a mask outlet valve 414*a*, which is configured for a one-way flow of air out of the face mask 130. Another exhalation hole is operably coupled to a mask outlet valve 414*b* with same configuration as mask outlet valve 414*a*.

In some other embodiments, the mask body 420 includes a mask inlet valve operably coupled to the inhalation hole 428. The mask inlet valve is configured for a one-way flow of air into the face mask 130. As the airflow generated by the air flow system may have a larger air volume than the air intake by the user, the mask inlet valve can provide a path for the excessive air to leave the mask body 420 to balance the air pressure within, increasing the level of comfort of the user. The one-way mask inlet valve can also prevent ambient air from entering the mask body 420. In some embodiments, the mask body 420 does not include a mask inlet valve and the positive pressure generated by the air flow system 120 ensures that air flows from the enclosed container into the face mask 130 through the tube 140. In some embodiments, the mask body 420 includes only one exhalation hole. In some embodiments, the mask body 420 may have more than two exhalation holes.

In this embodiment, the mask shell 410 has an inhalation opening 416 to allow tube 140 to engage with the inhalation hole 428 of the mask body 420 via the connector assembly 442. The mask shell 410 further includes two exhalation openings 412*a* and 412*b* arranged in positions that correspond to the position of the exhalation holes 426 of the mask body 420 to allow air exhausted by the user to be released to outer environment. In some embodiments, the mask shell 410 further includes two slots 415 for connecting a mask restraint strap (not shown) that extends around the user's head and holds the face mask 130 adjacent to the user's face. In other embodiments, the face mask 130 may not include a mask shell 410 but only the mask body 420.

Now turning to the operation of the respirator 100 described above. When the removable filter case 110 is inserted into chamber 122 of the enclosed container 120, an electrical connection between the battery 240 of the removable filter case 110 and the electrical connection port 370 is established to provide power to operate the air flow system 120. When the air flow system 120 is switched on, a flow of air is generated by the blower 311. As a result, ambient air enters the chamber 122 via the air inlets 321*a-h*, passes through the filters 220 and 230 housed in the removable filter case 110, flows through the blower assembly 310, exits the container 121 via the air outlet 322 and passes to the tube 140 and subsequently enters the face mask 130 via the inhalation hole 428 to supply filtered air to a user. Air exhausted by the user is released to outer environment via the exhalation holes 426 of the face mask 130.

In some embodiments, at least one of the filters 220 and 230 is a porous filter comprising a filtration material. When the flow of air passes through the porous filter, at least one contaminant in the flow of air is adsorbed by the porous filter. In some embodiments, at least one of the filters 220 and 230 is a mechanical filter. When the flow of air passes through the mechanical filter, particles and at least one pathogen in the flow of air are captured by the mechanical filter.

In some embodiments as described earlier, the air flow system 100 may include an oxidant generator configured to produce at least one oxidant. The oxidant generator is positioned before the filters 220 and 230 along the direction of the flow of air, such that after the flow of air passes the oxidant generator, the at least one oxidant produced and the at least one contaminant in the flow of air are simultaneously adsorbed by filtration material of the porous filter. The filtration material of the porous filter secures the adsorbed contaminant and oxidant into a confined space, and provides an active sites in which the oxidant can more effectively react with the contaminant. This catalyzes an oxidation reaction between the oxidant and the contaminant to promote decomposition of the contaminant on the porous filter. The oxidation reaction facilitates the continuous regeneration of the porous filter, resulting in a much extended filter life or even a perpetual use of the porous filter. As used herein and in the claims, "regenerate", "regenerated" or "regeneration" refers to restoration of the porous filter to a state that is free from the contaminant or has a lower level of the contaminant than before.

In some embodiments, the oxidant promotes disinfection of the pathogen in the flow of air and on the mechanical filter, thereby ensuring that the mechanical filter is safe to dispose.

Example 2

Respirator with Circulating Air Flow

Figure 5:
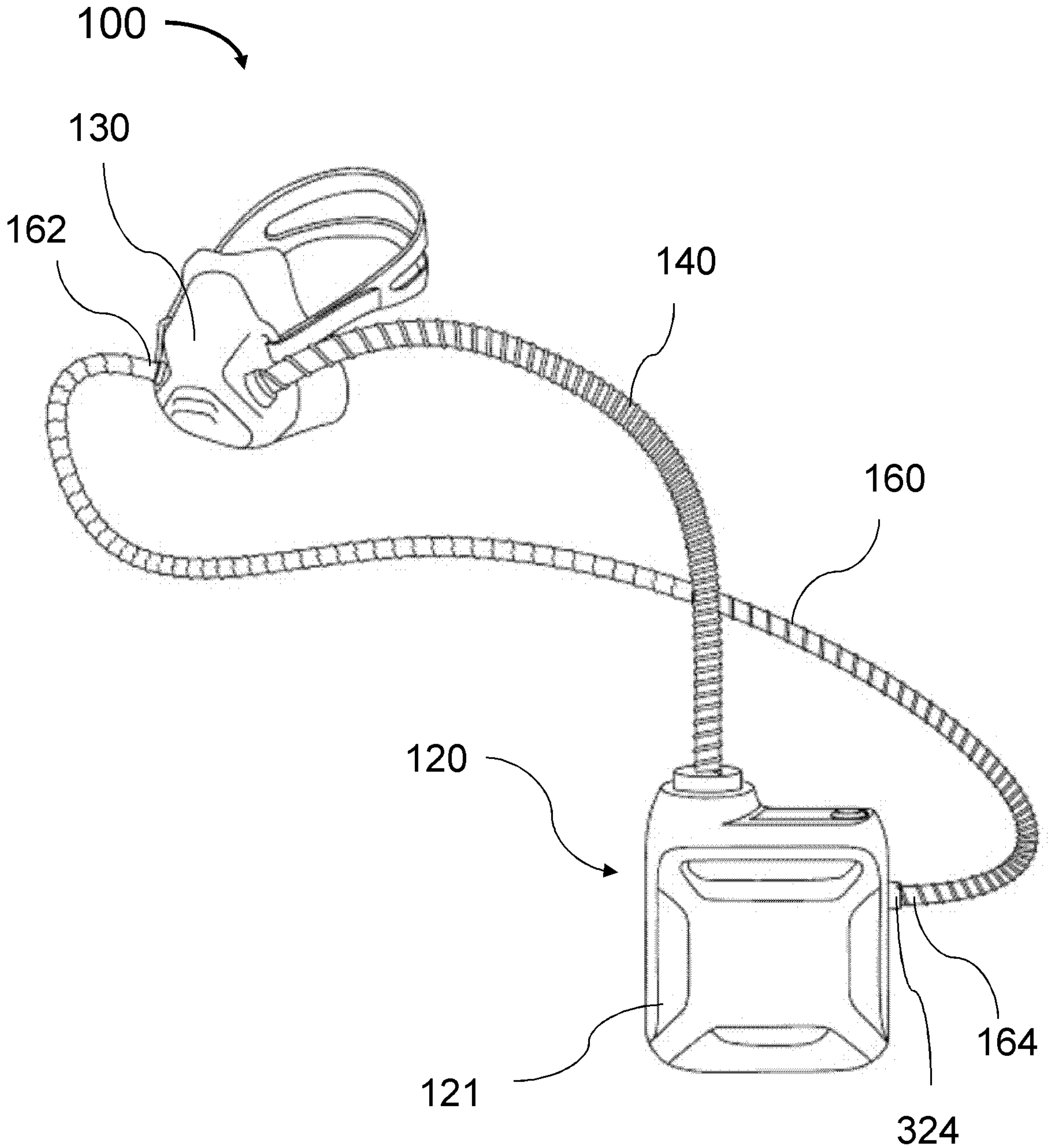
FIG. 5 is a perspective view of a respirator in accordance with an example embodiment.

Referring now to FIG. 5, which shows another example embodiment of a respirator 100. Similar to the example embodiment as described in FIG. 1, the respirator 100 comprises a face mask 130, an air flow system 120 including an container 121 and a tube 140 connecting the container 121 to the face mask 130, and at least one filter and/or removable filter case (not shown) housed in the container 121. In this example embodiment, the air flow system 120 further includes a second tube 160 connecting the face mask 130 to the container 121. The second tube 160 has a first end 162 adapted to be connected to the face mask 130 and a second end 144 adapted to be connected to the container 121. The second tube 160 is provided to allow an exhaled air to be delivered from the face mask 130 to the container 121.

Figure 6:
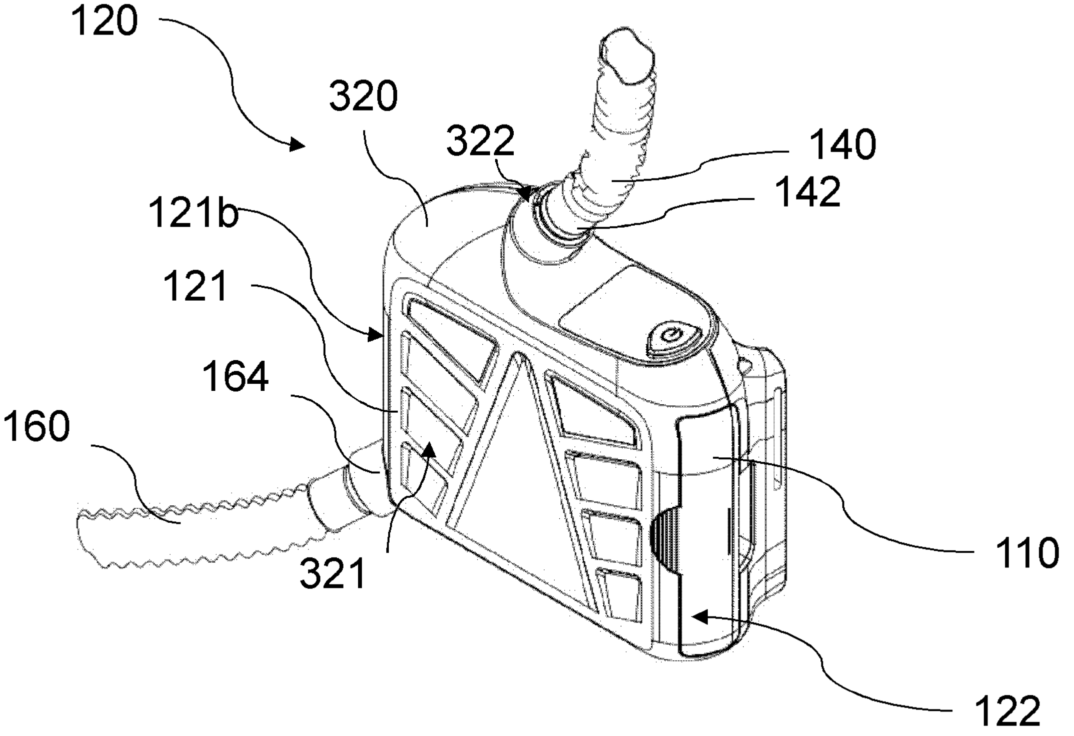
FIG. 6 is a perspective view of an air flow system in accordance with an example embodiment.

FIG. 6 shows a perspective view of the container 121 and a portion of the tube 140 and the second tube 160 of the air flow system 120 in accordance with the example embodiment as illustrated in FIG. 5. In this example embodiment, the container 121 includes all components as described in the example embodiment in FIG. 3, including a chamber 122 configured to accommodate the removable filter case 110, and an air outlet 322 connected to the first end 142 of the tube 140. For ease of description, tube 140 is called the first tube. In this example embodiment, the container 121 further comprises an exhaled air inlet 164 disposed on the bottom of the closed end 121*b* of the front cover 320. The second end 164 of the second tube 160 is connected to the container 121 via the exhaled air inlet 164 to allow the exhaled air to flow into the chamber 122 of the container 121. This configuration enables the exhaled air to be filtered when passing through the filters 220 and 230 in the removable filter case 110. The filtered exhaled air is then recirculated into the air flow system 120 along with ambient air. In some embodiments, the control unit of the air flow system 110 is configured to control the percentage of the ambient air entering the air flow system 110.

Figure 7A:
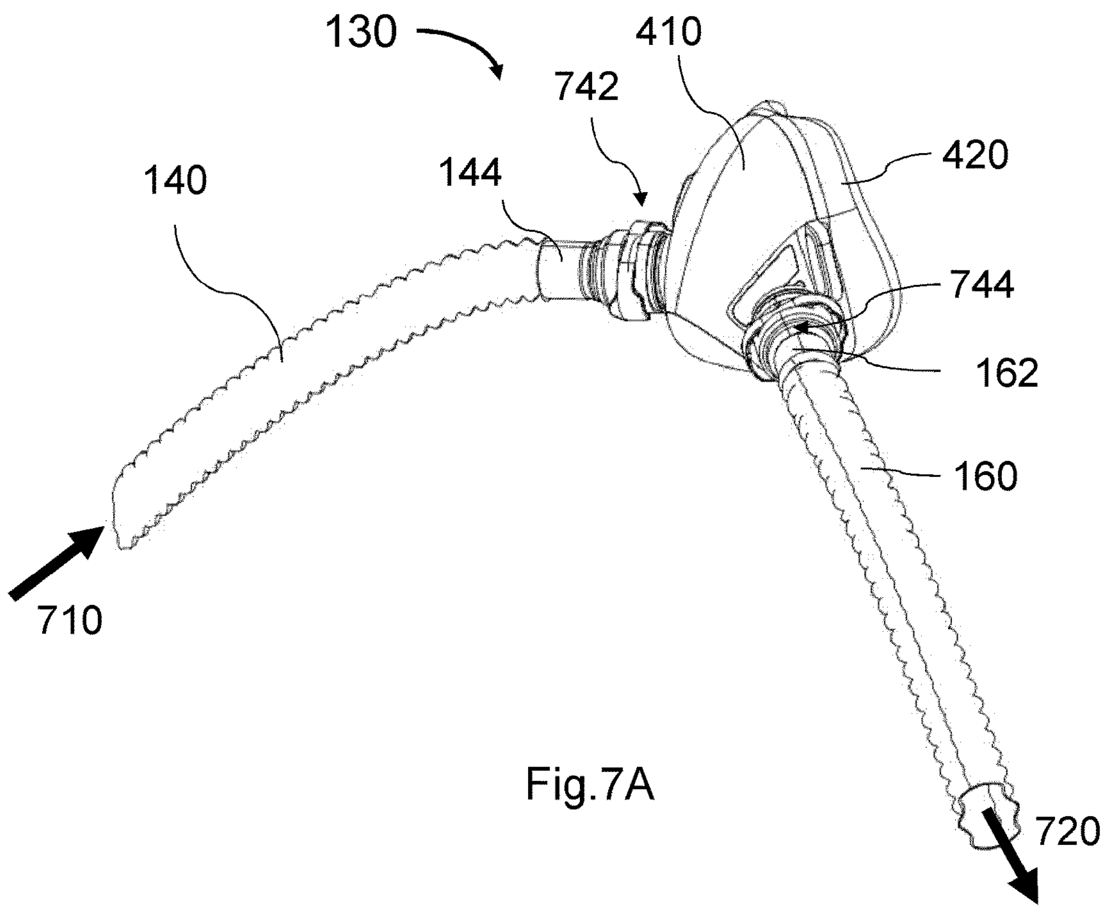
FIG. 7A is a perspective view of a face mask in accordance with an example embodiment.
Figure 7B:
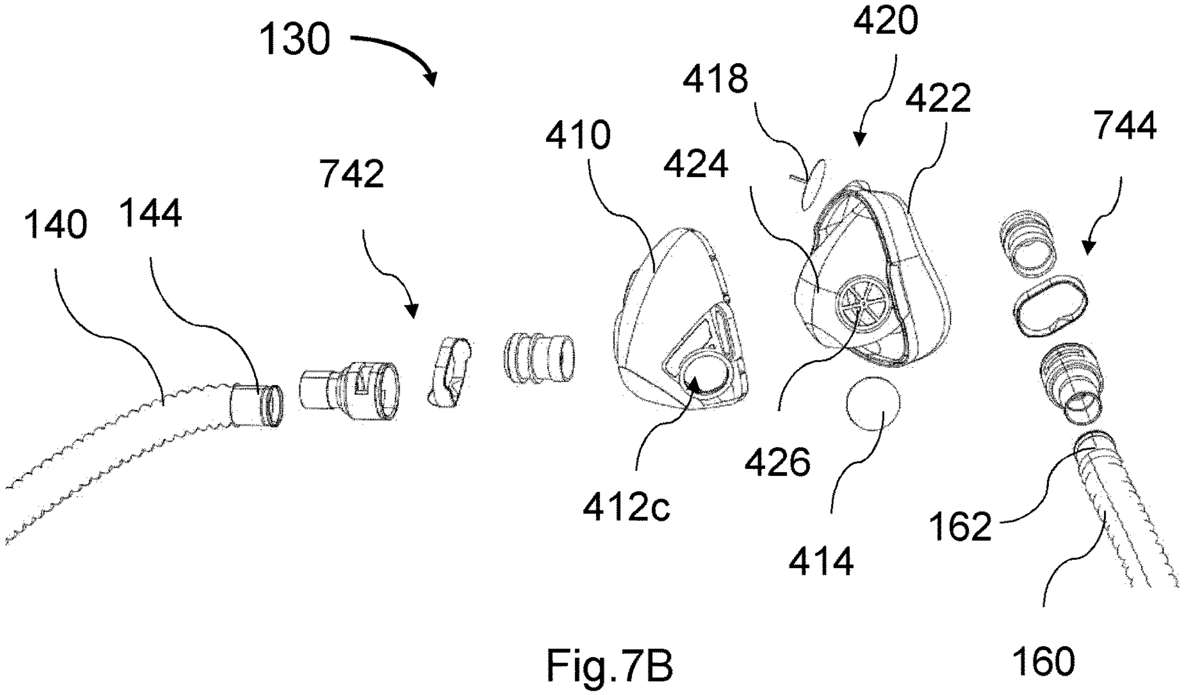
FIG. 7B is schematic exploded view of a face mask according to the same example embodiment as illustrated in FIG. 7A.

FIGS. 7A and 7B show the face mask 130 as shown in FIG. 5 and a portion of tube 140 and the second tube 160 connecting with the face mask 130. Similar to the example embodiment as illustrated in FIGS. 4A and 4B, the face mask 130 includes a mask shell 410 and a mask body 420. The mask body 420 has a nasal portion 424 and a face-contacting portion 422. In this example embodiment, the face mask 130 includes an inhalation hole (not shown) and an exhalation hole 426 provided on each lateral side of the nasal portion 424 of the mask body 420. The inhalation hole is removably engaged with the second end 144 of tube 140 through a connector assembly 742. The mask body 420 includes a mask inlet valve 418 operably coupled to the inhalation hole, which is configured for a one-way flow of air into the face mask 130. The exhalation hole 426 is removably engaged with the first end 162 of tube 160 through a connector assembly 744. The exhalation hole 426 is operably coupled to a mask outlet valve 414, which is configured for a one-way flow of air out of the face mask 130.

In this embodiment, the mask shell 410 has an inhalation opening (not shown) to allow tube 140 to engage with the inhalation hole (not shown) via the connector assembly 742, and an exhalation opening 412*c* to allow the second tube 160 to engage with the exhalation hole 426 via the connector assembly 744.

The direction of air flow is shown in FIG. 7A. Arrow 710 indicates the direction of air flowing from the first tube 140 into the face mask 130 via the inhalation hole (not shown), and arrow 720 indicates the direction of air flowing out of the face mask 130 via the exhalation hole 426.

Now turning to the operation of the respirator 100 described above. When the removable filter case 110 is inserted into chamber 122 of the container 121, an electrical connection between the battery 240 of the removable filter case 110 and the electrical connection port 370 is established to provide power to operate the air flow system 120. When the air flow system 120 is switched on, a flow of air is generated. As a result, a certain percentage of ambient air enters the chamber 122 via the air inlets 321, passes through the filters 220 and 230 housed in the removable filter case 110, exits the container 121 via the air outlet 322 and passes to the first tube 140 and enters the face mask 130 via the inhalation hole to supply filtered air to a user. Air exhausted by the user flows out of the face mask 130 via the exhalation holes 426, passes to the second tube 160, enters the container 121 via the exhaled air inlet 164 and passes through the filters 220 and 230 in the removable filter case 110. The filtered exhaled air is then recirculated into the air flow system 120. As a result, the flow of air generated by the air flow system 120 contains the filtered exhaled air and also a certain percentage of ambient air that continuously flows into the air flow system 120.

In some embodiments, the face mask 130 includes a second outlet valve (not shown) configured for a one-way flow of air out of the face mask to the outer environment, such that some air exhausted by the user is not recirculated back into the air flow system 120 but is released to outer environment instead.

In some embodiments, at least one of the filters 220 and 230 is a porous filter comprising a filtration material. When the flow of air passes through the porous filter, at least one contaminant in the flow of air is adsorbed by the porous filter. In some embodiments, at least one of the filters 220 and 230 is a mechanical filter. When the flow of air passes through the mechanical filter, particles and at least one pathogen in the flow of air are captured by the mechanical filter.

Example 3

Decontamination Device

Figure 8A:
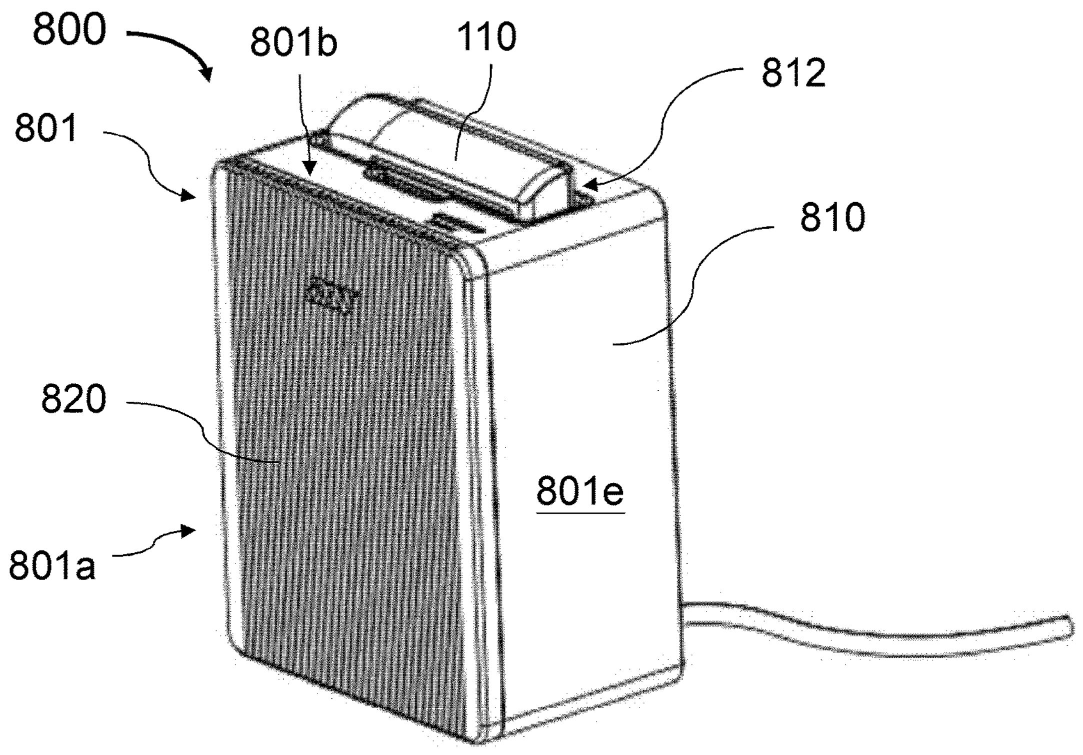
FIG. 8A is a perspective view of a decontamination device in accordance with an example embodiment.
Figure 8B:
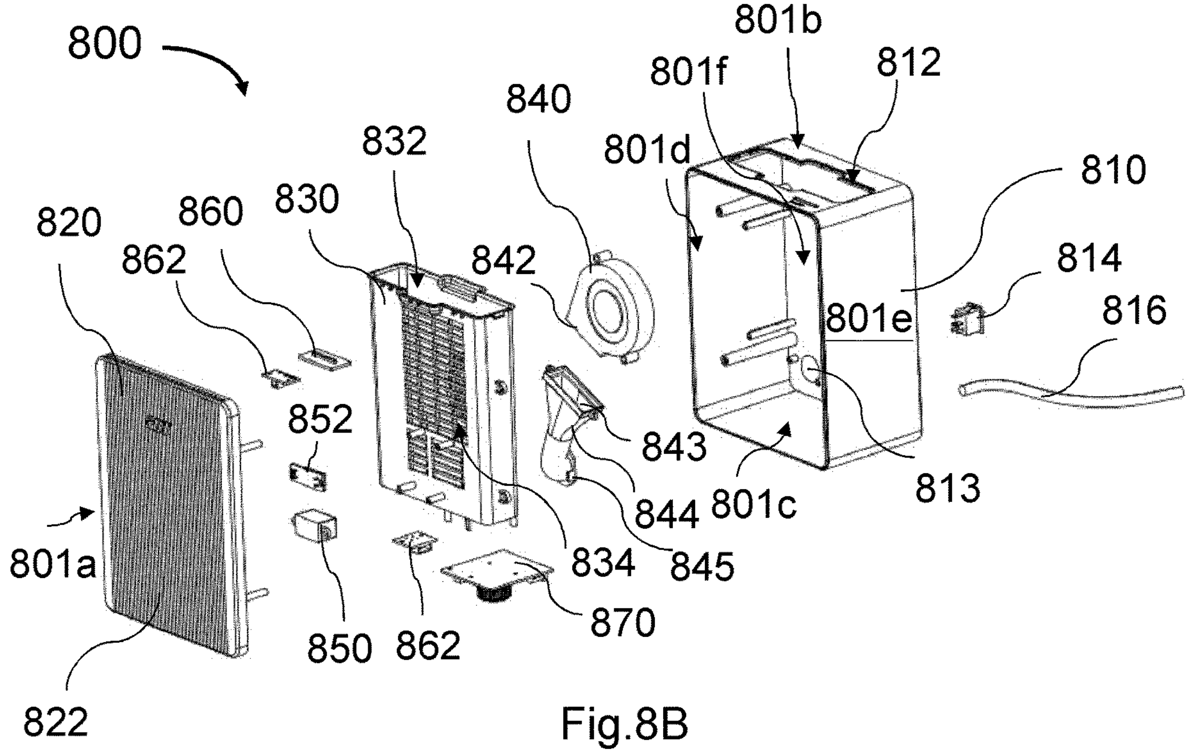
FIG. 8B is schematic exploded view of a decontamination device according to the same example embodiment as illustrated in FIG. 8A.

FIGS. 8A and 8B show the perspective view and exploded view of a decontamination device 800 respectively. The decontamination device 800 is configured to removably receive a removable filter case. FIG. 8A shows the decontamination device 800 with the removable filter case 110 inserted therein.

The decontamination device 800 has a housing 801 formed in a substantially vertical rectangular shape. The housing 801 has a front shell 820 and a back shell 810 coupled to each other to define an enclosed interior space. As shown in FIGS. 8A and 8B, the front shell 820 forms a front wall 801*a* of the housing 801, and the back shell 810 forms a back wall 801*f*, a top wall 801*b*, a bottom wall 801*c*, a side wall 801*d* and an opposing side wall 801*e* of the housing 801. For ease of description, the direction towards the side wall 801*d* is called left and direction away from the side wall 801*d* is called right. The front shell 820 is substantially flat and perforated with a plurality of slits 822 run vertically down the front shell 820 to allow air to pass through the front shell 820 into the housing 801. An opening 812 is provided on the top surface 801*b* of the back shell 810 to allow the removable filter case 110 to be inserted into the decontamination device 800. An exhaust hole 813 is provided on the back surface 801*f* of the housing 801 to allow air to exit the housing 801.

The decontamination device 800 further includes a filter cage 830, a blower 840, an oxidant generator 850 and a charging unit 862 housed within the enclosed interior space in the housing 801. The filter cage 830 has a substantially vertically rectangular shape defining a cavity therein for receiving the removable filter case 110. The top of the filter case is an open end with a slot 832 provided thereof such that the removable filter case 110 can be vertically inserted into the filter cage 830. The front of the filter cage 830 is provided with a plurality of air entrance openings 834 to allow air to enter the cavity, and the back of the filter cage is provided with an air exit opening (not shown) to allow air to leave the cavity. Referring to both FIG. 2A and FIG. 8A, when the removable filter case 110 is inserted into the filter cage 110, the left side surface 210*d* of the removable filter case 110 is facing the bottom of the filter cage 830, and the front surface 210*a* of the removable filter case 110 is facing the air entrance openings 834 of the filter cage 830.

In this embodiment, the blower 840 is positioned at the back of the filter cage 830 and is fluidly connected with the air exit opening (not shown) of the filter cage 830. The blower 840 is housed in a blower frame having a circular perimeter and an opening 842 connected to an air-duct 844. The air-duct 844 has an end 843 connected to the opening 842 and another end 845 connected to the exhaust hole 813 of the back shell 810. The blower 840 is configured to generate an airstream such that ambient air enters the housing 801 through the slits 822, passes through the filter cage 830, flows through the blower 840, and exits the housing 801 through the air-duct 844 connected to the exhaust hole 813.

When the removable filter case 110 containing the filter is inserted into the filter cage 830, the removable filter case 110 is positioned directly before the blower 840 along the direction of the airstream. As a result, the airstream generated by the blower 840 passes through the filter housed in the removable filter case 110 before flows through the blower 840.

The oxidant generator 850 is positioned in front of the air entrance openings 834 of the filter cage 830 such that when the removable filter case 110 is inserted into the filter cage 830, the oxidant generator 850 is situated before the removable filter case 110 along the direction of the airstream. The oxidant generator 850 is configured to produce at least one oxidant. In some embodiments, the entire enclosed interior space of the housing 801 is filled with the at least one oxidant when it is released by the oxidant generator 850. In some embodiments, the oxidant generator 850 is an ozone generator and the oxidant is ozone. In some other embodiments, the oxidant generator 850 is a hydroxyl radical generator and the oxidant is one or more hydroxyl radicals. In some other embodiments, the oxidant generator 850 is an ion generator and the oxidant is one or more ions. In some other embodiments, the oxidant is ozone, one or more hydroxyl radicals, one or more ions or a combination thereof.

In some other embodiments, the blower 840 may also be fitted in front of the filter cage 830 and the oxidant generator 850, such that when the removable filter case 110 is inserted into the filter cage 830, the blower 840 is positioned before the removable filter case 110 and the oxidant generator 850 along the direction of the airstream. As a result, the airstream generated by the blower 840 will first flow through the blower 840, pass through the oxidant generator 850 and blow into the filter housed in the removable filter case 110.

In this embodiment, the decontamination device 800 further comprises a control unit 870 contained in the housing 801. The control unit 870 is electrically connected with the blower 840, the charging unit 862, and the oxidant generator 850. An electrical connector 852 is optionally provided to facilitate electrical connection between the oxidant generator 850 and the control unit 870. The control unit 870 is also in electrical connection with a power supply unit configured to supply power to operate the decontamination device. In this embodiment, the power supply unit is a power cable 816 electrically connected with an external power source (not shown). The control unit 351 is configured to perform one or more of the following: a. switch on and switch off the decontamination device; b. detect the power of the battery 240; c. adjust a speed of the airstream; d. control a rate of oxidant production by the oxidant generator 850; and e. control and monitor an operation of the decontamination device 800. In some embodiments, the control unit 870 may include one or more oxidant sensor to monitor the level of oxidant. Once the oxidant level exceeds a certain amount, the control unit 870 will instruct the oxidant generator to stop generating the oxidant.

In this embodiment, the charging unit 862 is attached to the bottom of the filter cage 830. The charging unit 862 is electrically connected with the control unit 351 or directly with the power cable 816. Referring to both FIG. 2B and FIG. 8B, when the removable filter case 110 is inserted into the cavity of filter cage 830, an electrical connection is established between the charging unit 862 and the battery 240 via the electrical connector 270 of the removable filter case 110. The charging unit 862 is configured to provide power to recharge the battery 240 through the electrical connection.

In this embodiment, the decontamination device 800 further includes a switch 814 disposed on the back surface 801*f* of the housing 801. The switch 814 is electrically connected to the battery 240 (not shown) and/or the control unit 351 and configured to switch on or switch off the decontamination device 800.

In this embodiment, the decontamination device 800 further comprises a power detection circuit 862 configured detect the power of the battery 240, and a display unit 860 configured to display information of the status of the decontamination device 800, such as the power of the battery 240, speed of the blower 850, rate of the airstream etc. The display unit 352 is disposed on the top surface 801*b* of the housing 801. The display unit 860 is electrically connected to the power detection circuit 862 and/or the control unit 870. In some embodiments, the display unit 450 can be either a liquid-crystal display (LCD), Light-Emitting Diode (LED) or other kind of display.

In some other embodiments, the decontamination device 800 may include two separate compartments that are fluidly connected with each other. The removable filter cage 830 and the oxidant generator 850 may be housed in a first compartment, and the blower 840 and the air duct 844 may be housed in a second compartment. In some embodiments, the first compartment may be positioned in front of the second compartment. As a result, the airstream generated by the blower 840 will first flow through the first compartment and pass to the second compartment. In some other embodiments, the first compartment may be positioned at the back of the second compartment. As a result, the airstream generated by the blower 840 will first flow through the second compartment and pass to the first compartment. In some embodiments, the first compartment and the second compartment are individual parts that can be separated from each other, and the positions of the first compartment and the second compartment are interchangeable. Optionally, the first compartment and/or the second compartment may have a front shell perforated with a plurality of slits to allow air to pass through the front shell into the first compartment and/or the second compartment.

Now turning to the operation of the decontamination device 800 described above. The removable filter case 110 in this example embodiment is the same removable filter case 110 as described in FIGS. 2A and 2B having a mechanical filter 220 and a porous filter 230. The removable filter case 110 is removed from a respirator after being used for a certain period of time. At least one contaminant is adsorbed by the porous filter 230 and at least one pathogen in the flow of air is captured by the mechanical filter.

When the removable filter case 110 is inserted into the filter cage 830 of the decontamination device 800, the electrical connection established between the battery 240 of the removable filter case 110 and the charging unit 870 provides power to recharge the battery 240. At the same time, the blower 850 generated an airstream such that air enters the enclosed interior space of the housing 801. The airstream passes the oxidant generator 850 positioned in front of the filter cage 830, carrying with it the at least one oxidant produced by the oxidant generator 850 before entering the filter cage 830 containing the removable filter case 110. The filtration material of the porous filter catalyzes an oxidation reaction between the oxidant and the contaminant to promote decomposition of the contaminant on the porous filter. The oxidation reaction facilitates the regeneration of the porous filter such that the porous filter can be free from contaminant and be continuously reused. The oxidant also promotes disinfection of the pathogen on the mechanical filter, thereby ensuring that the mechanical filter is safe to dispose. The airstream that passes through the removable filter case will then flow into the blower 840 and exit the housing 801 through the air-duct 844 connected to the exhaust hole 813.

In some embodiments, the decontamination device 800 is a separate device that is not connected to the respirator 100. In some embodiments, the decontamination device 800 is configured to receive a porous filter and/or a mechanical filter without a removable filter case 110.

Example 4

Decontamination Device with Multiple Filter Cages

Figure 9A:
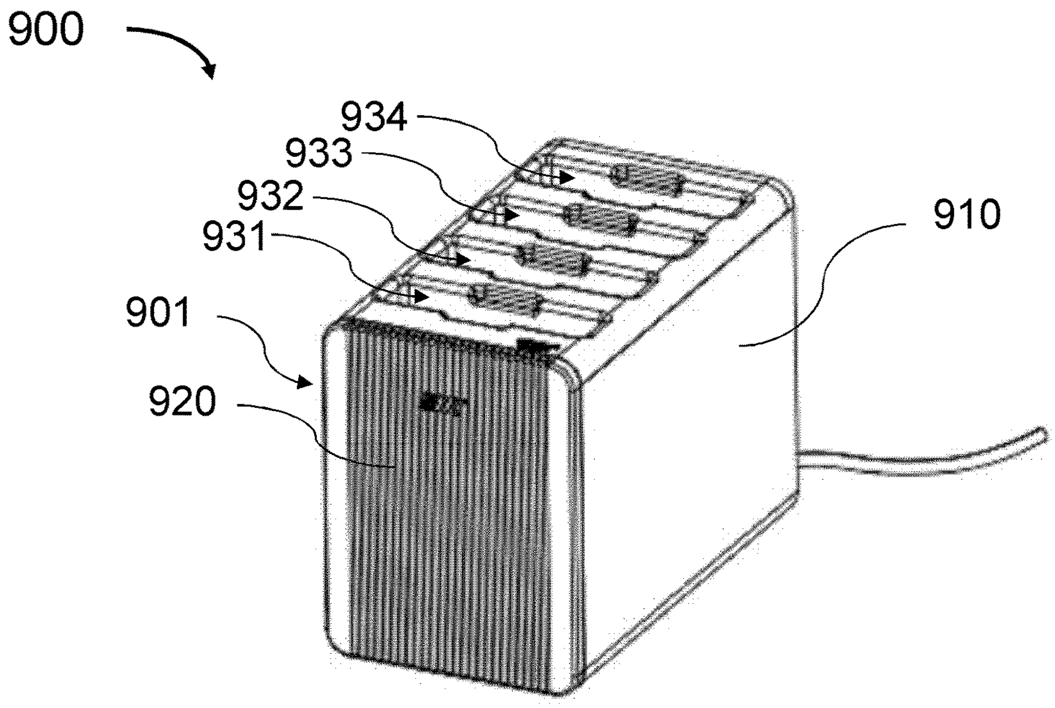
FIG. 9A is a perspective view of a decontamination device in accordance with an example embodiment.
Figure 9B:
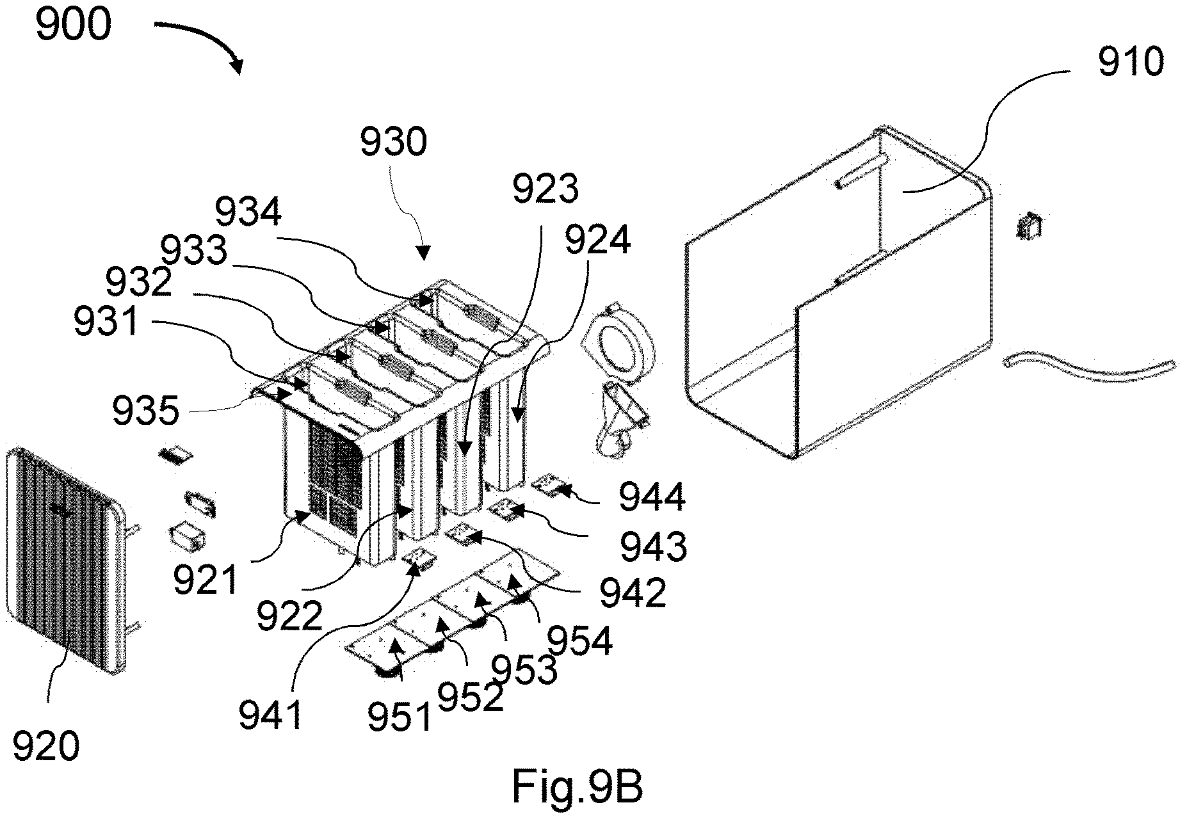
FIG. 9B is schematic exploded view of a decontamination device according to the same example embodiment as illustrated in FIG. 9A.

Referring now to FIGS. 9A and 9B, which shows another example embodiment of the decontamination device 800. In this embodiment, the decontamination device 800 is configured to removably receive four removable filter cases. The decontamination device 800 has a housing 901 formed in a substantially vertical rectangular shape. The housing 901 has a front shell 920 and a back shell 910. For ease of description, the direction towards the front shell 820 is called front, and the direction away from the front shell 820 is called back. The front shell 920 forms a front wall of the housing 901, and the back shell 910 forms a back wall, a bottom wall and two side walls of the housing 801. An opening is provided on the top of the back shell 910.

In this embodiment, the decontamination device 800 has a filter cage rack 930 contained in the housing 901. The filter cage rack 930 has four filter cages 921, 922, 923 and 924 arranged parallel to each other from front to back and linked together by a top plate 935. When the filter cage rack 930 is assembled together with the front shell 920 and the back shell 910, the top plate 935 forms a top wall of the housing 901 such that an enclosed interior space of the housing 901 can be defined.

Each filter cage has a substantially vertically rectangular shape defining a cavity therein for receiving a removable filter case 110. The top plate 935 has four slot 931, 932, 933 and 934 provided thereof such that the removable filter cases can be vertically inserted into the filter cages 921, 922, 923 and 924 respectively. Similar to the filter cage 830 in FIG. 8B, the front of each filter cage is provided with a plurality of air entrance openings to allow air to enter the cavity, and the back of each filter cage is provided with an air exit opening to allow air to leave the cavity.

In this embodiment, the decontamination device 800 has four charging units 941, 942, 943 and 944 attached to the bottom of the filter cages 921, 922, 923 and 924 respectively. The decontamination device 800 also has four control units 951, 952, 953 and 954 attached together with each other from front to back. The charging unit 941, 942, 943 and 944 are electrically connected with the control units 951, 952, 953 and 954 respectively. The charging units 941, 942, 943 and 944 is configured to provide power to recharge the batteries of the removable filter cases when they are inserted in the filter cages 921, 922, 923 and 924 respectively through their respective electrical connections.

In this embodiment, the decontamination device 800 is configured to receive up to four removable filter cases at the same time. The filters contained in the four removable filter cases can be decontaminated and regenerated simultaneously when they are inserted into the decontamination device 800, and at the same time the batteries of the four removable filter cases are recharged. This arrangement will greatly improve the efficiency of the decontamination device 800. Advantageously, each of the removable filter cases can be removed from or inserted into the decontamination device 800 individually, providing a flexibility for a user when using the device.

In some other embodiments, the decontamination device 800 is configured to receive two removable filter cases and the filter rack 930 contains two filter cages. In some other embodiments, the decontamination device 800 is configured to receive three removable filter cases and the filter rack 930 contains three filter cages. In some other embodiments, the decontamination device 800 is configured to receive more than four removable filter cases and the filter rack 930 contains more than four filter cages. In some embodiments, the decontamination device 800 is configured to receive more than one porous filter and/or a mechanical filter without removable filter case 110.

In some other embodiments, the multiple filter cages of the decontamination device may be housed in separate compartments or modular filter cartridges that can be arranged into filter cartridge assemblies of various configurations by interconnecting the filter cartridges in a desired configuration. The modular filter cartridges can be fluidly communicated with each other. Each cartridge may house one or at least one filter cage, and may be sized and shaped as an individual, modular component that can be removably connected with the other component. As such, the relative position of each filter cartridge is interchangeable, and the decontamination device may be housed with one or a plurality of modular filter cartridges as required. Optionally, each compartment may have a front shell perforated with a plurality of slits to allow air to pass through the front shell into the compartment, and an exhaust hole disposed at the back of the compartment to allow air to leave the compartment and pass through an adjacent compartment positioned behind. In some embodiments, the blower and the air duct may be housed in a separate compartment in the decontamination device. A user can therefore add or remove any number of compartments from the decontamination device, or rearrange the relative position of each compartment in the decontamination device according to the user's preference.

Example 5

Air Purification System

One aspect provides an air purification system having a respirator 100 and a decontamination device 800 as described earlier.

In one embodiment, the respirator 100 includes a porous filter comprising a filtration material. When the air flow system of the respirator 100 is switched on, a flow of air is generated by the blower such that ambient air passes through the porous filter to the face mask. When the flow of air passes through the porous filter, at least one contaminant in the flow of air is adsorbed by the porous filter, such that the air entering the face mask is free from the contaminant.

The porous filter is removed from the respirator after being used for a certain period of time and inserted into the decontamination device 800, which is configured to removably receive the porous filter. The decontamination device includes an oxidant generator configured to produce at least one oxidant. In some embodiments, the decontamination device includes a blower configured to direct an airstream towards the porous filter. The airstream passes the oxidant generator positioned in front of the porous filter, carrying with it the at least one oxidant produced by the oxidant generator before passes through the porous filter. The filtration material of the porous filter catalyzes an oxidation reaction between the oxidant and the contaminant to promote decomposition of the contaminant on the porous filter. The oxidation reaction facilitates the regeneration of the porous filter such that the porous filter can be free from contaminant and be continuously reused.

In some embodiments, the filtration material have a pore size that permits absorption of both the contaminant and the oxidant. In some embodiments, the filtration material of the porous filter comprises zeolite having a pore size in the range of 2 Angstroms to 20 Angstroms.

In some embodiments, the air purification system includes more than one respirators 100. In some embodiments, the air purification system may have two, three or four respirators 100. In some embodiments, the decontamination device 800 is configured to removably receive more than one porous filter from more than one respirator to facilitate the decontamination and regeneration of more than one porous filter simultaneously.

In another embodiment, the respirator 100 of the air purification system includes a mechanical filter. When the air flow system of the respirator 100 is switched on, a flow of air is generated by the blower such that ambient air passes through the mechanical filter to the face mask. When the flow of air passes through the mechanical filter, at least one pathogen in the flow of air is adsorbed by the porous filter, such that the air entering the face mask is free from the pathogen.

The mechanical filter is removed from the respirator after being used for a certain period of time and inserted into the decontamination device 800, which is configured to removably receive the mechanical filter. In some embodiments, the decontamination device includes a blower configured to direct an airstream towards the mechanical filter. The airstream passes the oxidant generator positioned in front of the mechanical filter, carrying with it the at least one oxidant produced by the oxidant generator before passes through the mechanical filter. The oxidant promotes disinfection of the pathogen on the mechanical filter, thereby ensuring that the mechanical filter is safe to dispose.

In some embodiments, the decontamination device is configured to removably receive more than one mechanical filter from more than one respirator to facilitate the disinfection of more than one mechanical filter simultaneously.

In another embodiment, the respirator 100 of the air purification system includes a removable filter case 110. The removable filter case includes two filters and a rechargeable battery 240. The two filters include a mechanical filter and a porous filter comprising a filtration material.

When the removable filter case 110 is inserted into the container 121 of the air flow system 120, an electrical connection between the battery 240 of the removable filter case 110 and the electrical connection port 370 is established to provide power to operate the air flow system 120. When the air flow system 120 is switched on, a flow of air is generated by the blower such that ambient air passes through the removable filter case 110 through the two filters to the face mask. When the flow of air passes through the mechanical filter, at least one pathogen in the flow of air is adsorbed by the porous filter, such that the air entering the face mask is free from the pathogen. When the flow of air passes through the porous filter, at least one contaminant in the flow of air is adsorbed by the porous filter, such that the air entering the face mask is free from the contaminant.

The removable filter case is removed from the respirator after being used for a certain period of time and inserted into the decontamination device 800, which is configured to removably receive the removable filter case. In some embodiments, the decontamination device includes a blower configured to direct an airstream towards the removable filter case. The airstream passes the oxidant generator positioned in front of the removable filter case, carrying with it the at least one oxidant produced by the oxidant generator before passes through the two filters in the removable filter case. The filtration material of the porous filter catalyzes an oxidation reaction between the oxidant and the contaminant to promote decomposition of the contaminant on the porous filter. The oxidation reaction facilitates the regeneration of the porous filter such that the porous filter can be free from contaminant and be continuously reused. The oxidant also promotes disinfection of the pathogen on the mechanical filter, thereby ensuring that the mechanical filter is safe to dispose. At the same time, the charging unit of the decontamination device provides power to recharge the battery of the removable filter case.

Figure 10:
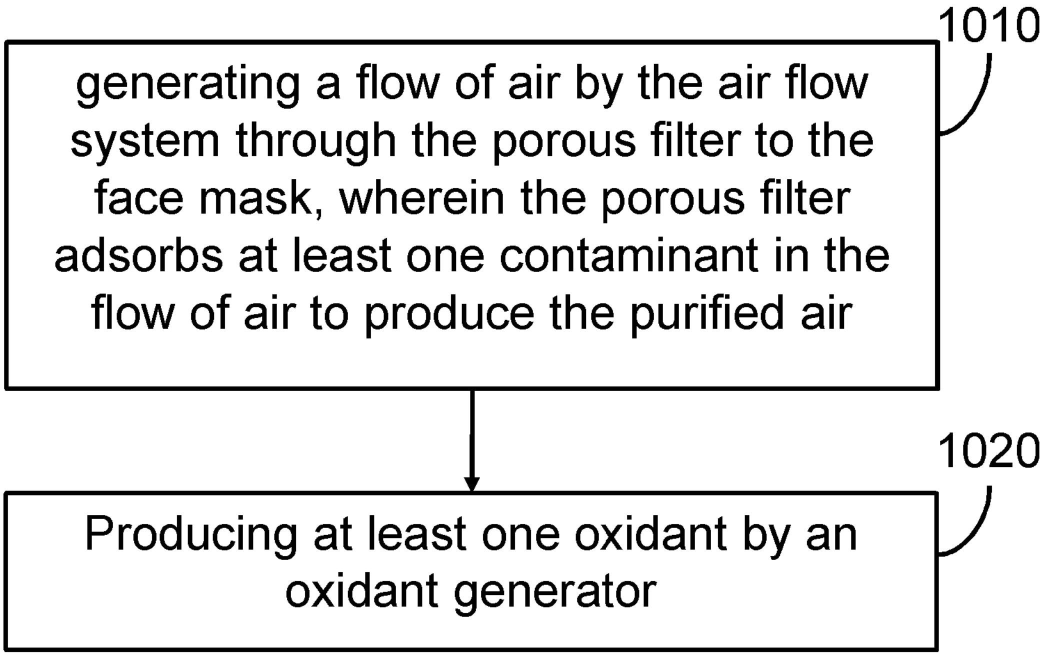
FIG. 10 shows a method of providing purified air to a user by an air flow system in accordance with an example embodiment.

FIG. 10 shows a method of providing purified air to a user by an air flow system in fluid communication with a porous filter comprising a filtration material and a face mask in accordance with an example embodiment.

Block 1010 states generating a flow of air by the air flow system through the porous filter to the face mask, wherein the porous filter adsorbs at least one contaminant in the flow of air to produce the purified air.

Block 1020 states producing at least one oxidant by an oxidant generator. The filtration material of the porous filter is capable of catalyzing an oxidation reaction between the oxidant and the contaminant to promote decomposition of the contaminant on the porous filter.

Figure 11:
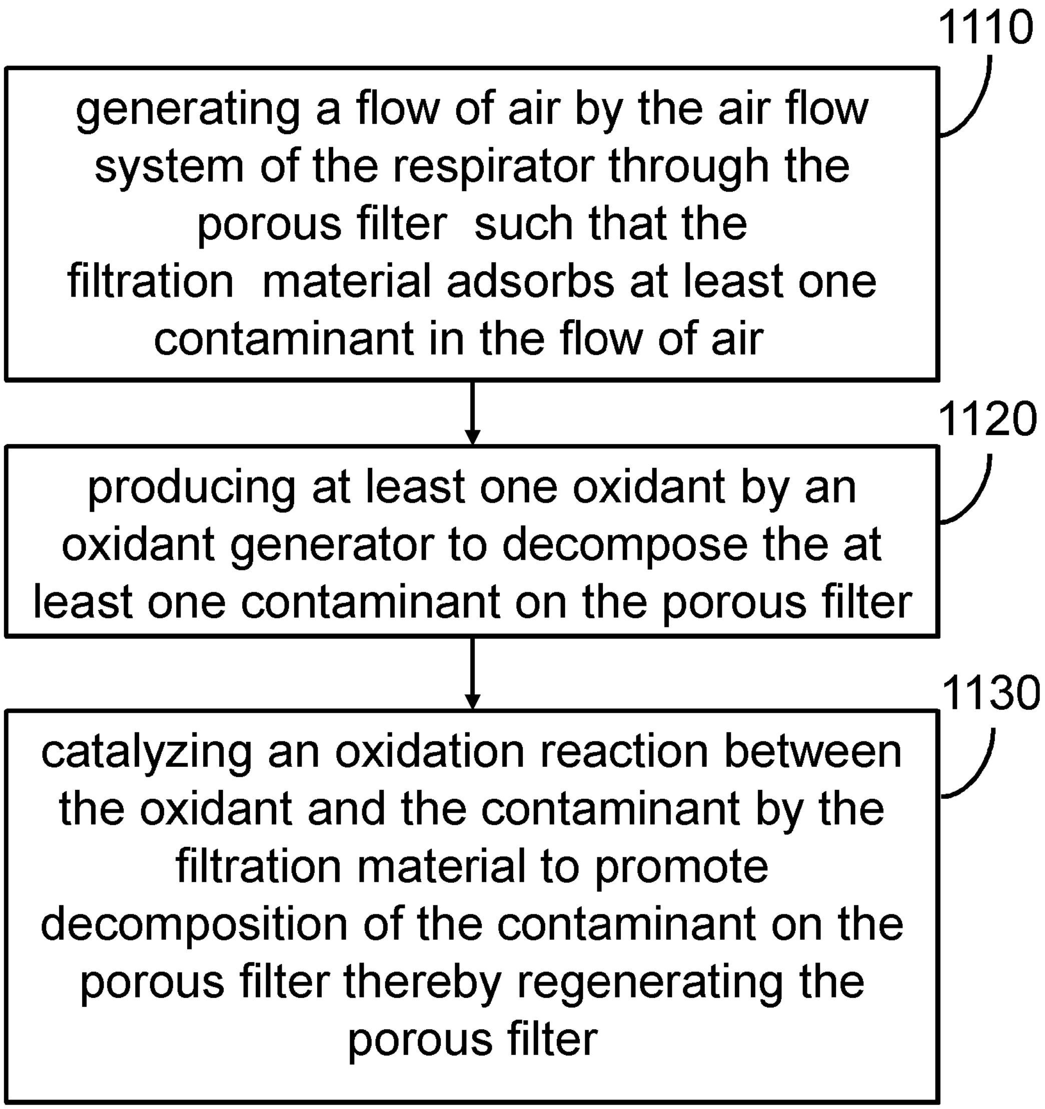
FIG. 11 shows a method of regenerating a porous filter using the air purification system as described above in accordance with an example embodiment.

FIG. 11 shows a method of regenerating porous filter using the air purification system as described above in accordance with an example embodiment.

Block 1110 states generating a flow of air by the air flow system of the respirator through the porous filter such that the filtration material adsorbs at least one contaminant in the flow of air.

Block 1120 states producing at least one oxidant by an oxidant generator to decompose the at least one contaminant on the porous filter.

Block 1130 states catalyzing an oxidation reaction between the oxidant and the contaminant by the filtration material to promote decomposition of the contaminant on the porous filter thereby regenerating the porous filter. The regenerated porous filter is free from contaminant and can be reused.

In some embodiments, the oxidation reaction is done in a separate decontamination device. In some embodiments, the method above further includes the step of removing the porous filter comprising the filtration material from the respirator and inserting it into the decontamination device.

Figure 12:
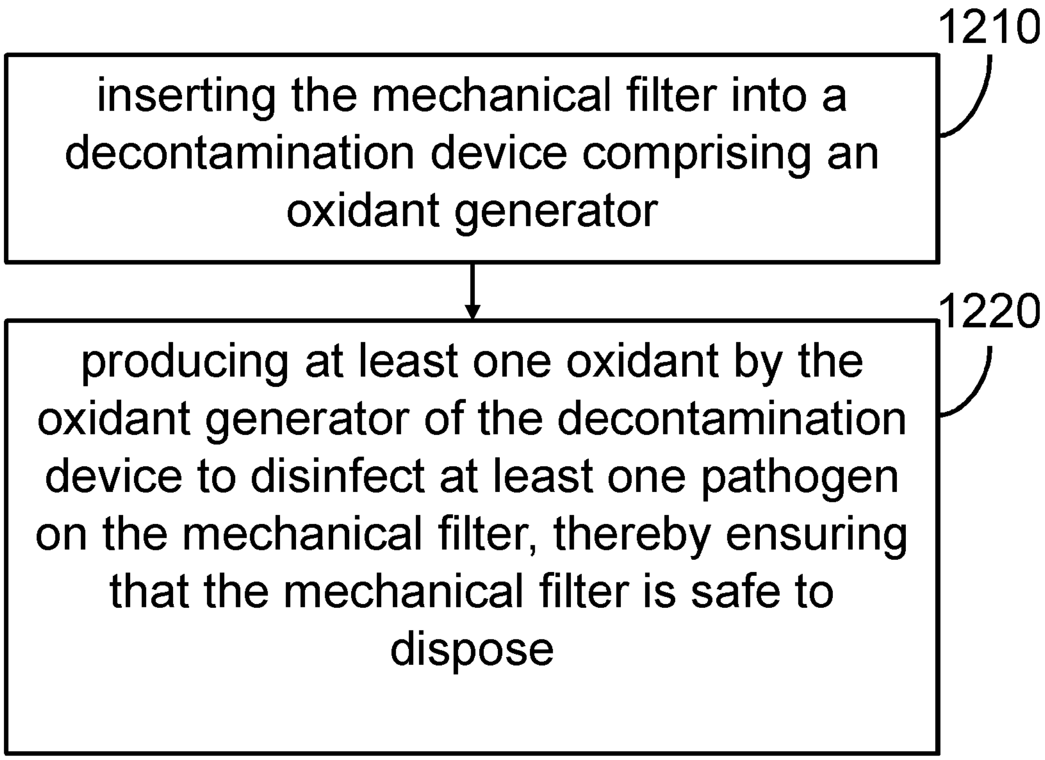
FIG. 12 shows a method of disinfecting a mechanical filter using the air purification system as described above in accordance with an example embodiment.

FIG. 12 shows a method of disinfecting a mechanical filter using the air purification system as described above in accordance with an example embodiment.

Block 1210 states inserting the mechanical filter into a decontamination device comprising an oxidant generator.

Block 1220 states producing at least one oxidant by the oxidant generator of the decontamination device to disinfect at least one pathogen on the mechanical filter, thereby ensuring that the mechanical filter is safe to dispose.

Example 6—Testing Specimens of Two Example Respirators

The various tests that are described in the following examples (Examples 7-11) are conducted on testing specimens of two example respirators, namely Respirator 1 and Respirator 2.

Respirator 1

Respirator 1 includes a face mask and an air flow system which includes an enclosed container that is in fluid communication with the face mask. In comparison with Respirator 2 as described below, Respirator 1 does not include a removable filter case provided therein, but includes a porous filter and a mechanical filter that are directly housed within the enclosed container and positioned before the blower along the direction of the flow of air. The structures and arrangements of the face mask and the tube in Respirator 1 are generally similar to Respirator 2. The cross-section area of the tube used is 0.0007 $m^2$.

Respirator 2

Respirator 2 includes a face mask and an air flow system which includes an enclosed container that is in fluid communication with the face mask. In comparison with Respirator 1 as described above, Respirator 2 includes a removable filter case which houses a porous filter, a mechanical filter and a battery, and the enclosed container further comprises a chamber to receive the removable filter case. The structures and arrangements of these components in Respirator 2 are generally the same with the respirator 100 as described in Example 1 and FIG. 1 above. The cross-section area of the tube used is 0.0007 $m^2$.

Table 1 summarizes the detailed configurations of the Respirator 1 and Respirator 2, respectively.

TABLE 1

| Configurations | Respirator 1 | Respirator 2 |
|---|---|---|
| Filter(s) configuration | Filter(s) is housed within the device | Filter(s) is housed in a removable filter case |
| Dimension | 6.3"(width) × 6.3"(height) × 3.46"(depth) | 8"(width) × 7"(height) × 2.75"(depth) |
| Maximum air volume reached by the blower | 119 L/min | 280 L/min |
| Battery capacity | 3200 mAh | 3200 mAh |
| Power Supply | 12 V DC/0.5 A | 12 V DC/0.5 A |
| Power Consumption | 2.5 W | 6 W |

Example 7—Measurement of Airflow Rates for the Respirator

To evaluate and compare the airflow rates of the testing specimens (Respirators 1 and 2) with different structural arrangements as described in Example 6 above, measurement was carried out to determine the air inflow rates and the air outflow rates of the two respirators.

Methods and Materials:

Instrument: Tenmars TM-4001

Environmental conditions: 25° C., around 50% Relative Humidity (RH)

Methods:

The blower speeds of the testing specimens (Respirators 1 and 2) were adjusted at Level 1 (low speed) and Level 2 (high speed). For each level, measurement on the air inflow rates was carried out by taking multiple sampling on different sampling points near the air inlets of the enclosed container of the testing specimens by Tenmars TM-4001 according to manufacturer's instructions. 8 different sampling points (sampling points 1-8 in Table 2) were taken for Respirator 1, whereas 11 different sampling points (sampling points 1-11 in Table 4) were taken for Respirator 2. Measurement on the air outflow rates was carried out by taking multiple sampling on different sampling points inside the face mask and/or near the enclosed container of the testing specimens. 11 different sampling points (sampling points 9-17 (taken inside the face mask) and sampling points 18-19 (taken near the enclosed container) in Table 3) were taken for Respirator 1, whereas 9 different sampling points (sampling points 12-20 (taken inside the face mask) in Table 5) were taken for Respirator 2.

Results:

Tables 2 and 3 summarize the air inflow rates and air outflow rates of Respirator 1 respectively. Tables 4 and 5 summarize the air inflow rates and air outflow rates of Respirator 2 respectively. The average air inflow rates of Respirator 1 is 0.56 m/s and 0.74 m/s at blower speed of Level 1 (low speed) and Level 2 (high speed), respectively, and that the average air outflow rate of Respirator 1 is 2.34 m/s and 2.84 m/s at blower speed of Level 1 (low speed) and Level 2 (high speed), respectively. The average air inflow rates of Respirator 2 is 0.65 m/s and 0.98 m/s at blower speed of Level 1 (low speed) and Level 2 (high speed), respectively, and that the average air outflow rate of Respirator 1 is 4.29 m/s and 6.67 m/s at blower speed of Level 1 (low speed) and Level 2 (high speed), respectively. The results indicated that the air inflow rates and the air outflow rates of Respirator 2 at both blower speeds are significantly higher than that of Respirator 1.

TABLE 2

Air inflow rates (m/s) of Respirator 1

| Sampling point | Blower speed Level 1 | Blower speed Level 2 |
|---|---|---|
| 1 | 0.56 | 0.81 |
| 2 | 0.51 | 0.67 |
| 3 | 0.49 | 0.62 |
| 4 | 0.48 | 0.74 |
| 5 | 0.69 | 0.86 |
| 6 | 0.57 | 0.74 |
| 7 | 0.56 | 0.74 |
| 8 | 0.63 | 0.71 |
| Average | 0.56 | 0.74 |

TABLE 3

Air outflow rates (m/s) of Respirator 1

| Sampling point | Blower speed Level 1 | Blower speed Level 2 |
|---|---|---|
| 9 | 2.47 | 2.93 |
| 10 | 1.34 | 2.31 |
| 11 | 2.52 | 2.87 |
| 12 | 2.12 | 2.69 |
| 13 | 2.6 | 3.31 |
| 14 | 2.18 | 2.56 |
| 15 | 2.66 | 3.11 |
| 16 | 2.54 | 3.16 |
| 17 | 2.98 | 3.43 |
| 18 | 2.02 | 2.31 |
| 19 | 2.26 | 2.52 |
| Average | 2.34 | 2.84 |

TABLE 4

Air inflow rate (m/s) of Respirator 2

| Sampling point | Blower speed Level 1 | Blower speed Level 2 |
|---|---|---|
| 1 | 0.67 | 0.97 |
| 2 | 0.71 | 0.98 |
| 3 | 0.61 | 0.88 |
| 4 | 0.66 | 0.99 |
| 5 | 0.83 | 1.12 |
| 6 | 0.62 | 0.89 |
| 7 | 0.46 | 0.89 |

TABLE 4-continued

Air inflow rate (m/s) of Respirator 2

| Sampling point | Blower speed | |
|---|---|---|
| | Level 1 | Level 2 |
| 8 | 0.56 | 1.07 |
| 9 | 0.82 | 1.27 |
| 10 | 0.62 | 0.81 |
| 11 | 0.58 | 0.9 |
| Average | 0.65 | 0.98 |

TABLE 5

Air outflow rate (m/s) of Respirator 2

| Sampling point | Blower speed | |
|---|---|---|
| | Level 1 | Level 2 |
| 12 | 4.78 | 6.38 |
| 13 | 4.59 | 5.94 |
| 14 | 3.8 | 5.28 |
| 15 | 3.8 | 6.5 |
| 16 | 4.43 | 7.24 |
| 17 | 4.77 | 6.48 |
| 18 | 3.85 | 5.49 |
| 19 | 4.1 | 7.68 |
| 20 | 4.5 | 9.06 |
| Average | 4.29 | 6.67 |

Calculation of Maximum air volume reached for the respirators

For each of the testing specimens, the maximum air volume reached was calculated by the following formula:

$$(\text{Max. air outflow rate})\times(\text{tube cross-section area})$$

The results of the maximum air volume reached were calculated as below:

$$2.84\ \text{m/s}\times0.0007\ \text{m}^2=0.001988\ \text{m}^3/\text{s}=119\ \text{L/min} \quad \text{Respirator 1:}$$

$$6.67\ \text{m/s}\times0.0007\ \text{m}^2=0.004669\ \text{m}^3/\text{s}=280\ \text{L/min} \quad \text{Respirator 2:}$$

In summary, the results above demonstrate that both example respirators have satisfactory levels of air flow rates but Respirator 2 has a significantly higher average air inflow rates, average air outflow rates and maximum air volume reached compared to Respirator 1.

Example 8: Particulate Matter (PM) Removal Efficiency

To evaluate and compare the Particulate Matter (PM) removal efficiencies of the testing specimens (Respirators 1 and 2) with different structural arrangements as described in Example 6 above, a test for PM removal efficiency was performed.

Materials and Methods:

Instrument: Met One Instruments, Aerocet 831

Environmental conditions: 25° C., around 50% Relative Humidity (RH)

Test Standards and Methods:

Test standard and method for Respirator 1: GB/T 18801-2015

The test was conducted in a confined test chamber with a standard volume of 3 $m^3$. Cigarette smoke was utilized as a surrogate source of air pollutants, which is a well-known indoor air pollutant with adverse health effects, therefore commonly used in air purifier testing standards, such as GB/T 18801-2015. In principle, such smoke contains aerosol particles, making it suitable for testing air purifier performance on solid phase pollutants.

Figure 13A:
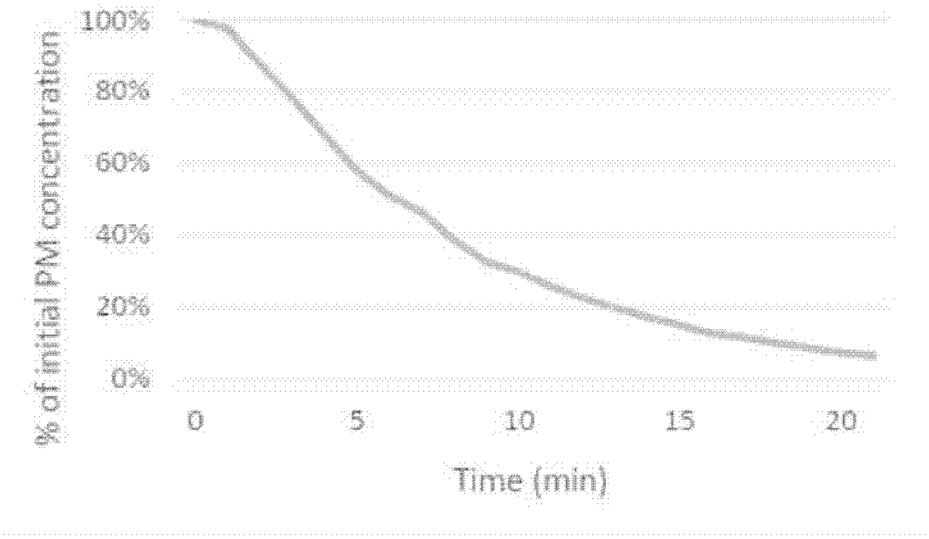
FIGS. 13A and 13B are charts showing the changes in percentage (%) of PM10 and PM2.5 concentrations respectively over time for the tests conducted with Respirator 1 in accordance with an example embodiment.
Figure 13B:
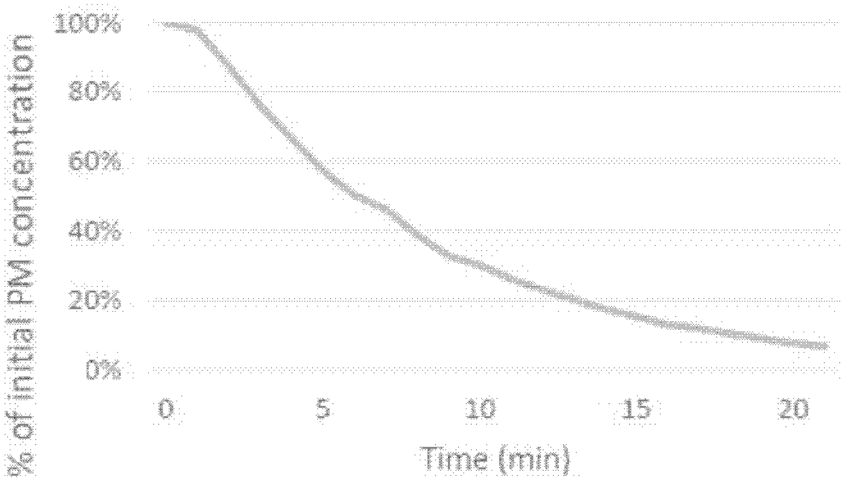

The test method was performed with the test procedures outlined in test standard GB/T 18801-2015. The test method involves separating the performance of the testing specimens from natural air cleaning, which incurred in indoor air known as "natural decay." For this, firstly, appropriate amount of the particle pollutant (generated via burning of a cigarette) was released into the test chamber with the testing specimens switched off and the gradual settling of the air contaminant was measured over time (20 mins). Then, the test was repeated with the contaminant at the same level and with the testing specimens switched on to measure a total air cleaning rate. The measurement of natural air cleaning was subtracted from the measurement of total air cleaning to provide the PM removal results of the cleaning by the testing specimens alone. In other words, the reported PM removal efficiency represents only the standalone performance of the testing specimens under test in terms of the ratio of the amount removed to the total amount of the pollutant present in the chamber. The results were subsequently converted into percentage values (shown as % in PM10 and PM2.5 concentrations compared to initial concentrations over time as shown in FIGS. 13A and 13B respectively).

The air contaminant particles are divided into two groups based on their diameters. Those with a diameter between 2.5 and 10 micrometers are called PM10, and those with a diameter smaller than 2.5 micrometers are called PM2.5.

Test Standard and Method for Respirator 2:

The test was conducted in a confined test chamber with a volume of 1 $m^3$. Similar to the test method for Respirator 1 as described above, cigarette smoke was utilized as a surrogate source of air pollutants.

The test method was modified from test standard GB/T 18801-2015 and resembles closely the test procedures outlined in GB/T 18801-2015 with the exception that a 1 $m^3$ confined chamber and longer testing duration were used in the test instead. Under this modified method, same procedures are performed to determine both the "natural decay" and "total air cleaning" performances, with the testing time prolonged to 40 mins. The results were obtained via subtracting the measurement of "natural decay" from the measurement of "total air cleaning" and the results were subsequently converted into percentage values (shown as % in PM10 and PM2.5 concentrations compared to initial concentrations over time as shown in FIGS. 14A and 14B respectively).

Results:

FIGS. 13A and 13B show the changes in percentage (%) in PM10 and PM2.5 concentrations respectively over time for the test conducted with Respirator 1. The results show that Respirator 1 achieves a PM removal efficiency of 93.46% for PM10 and 93.38% for PM2.5 at the end of the test.

Figure 14A:
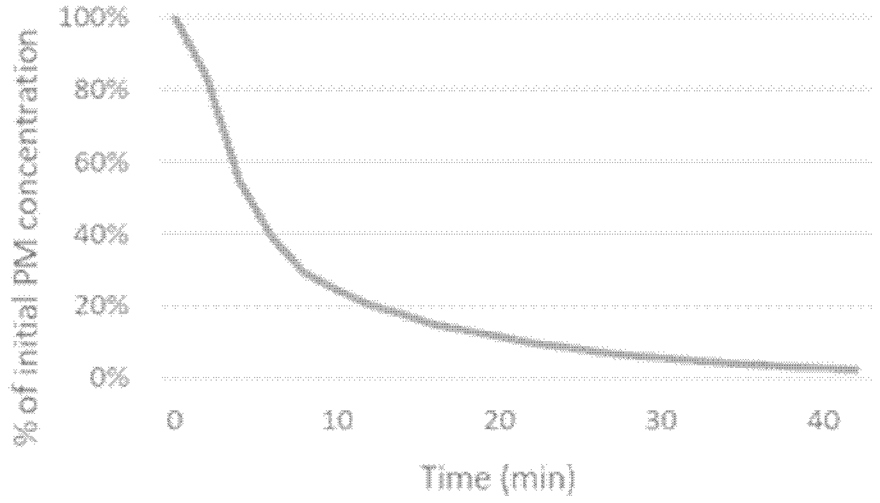
FIGS. 14A and 14B are charts showing the changes in percentage (%) in PM10 and PM2.5 concentrations respectively over time for the tests conducted with Respirator 2 in accordance with an example embodiment.
Figure 14B:
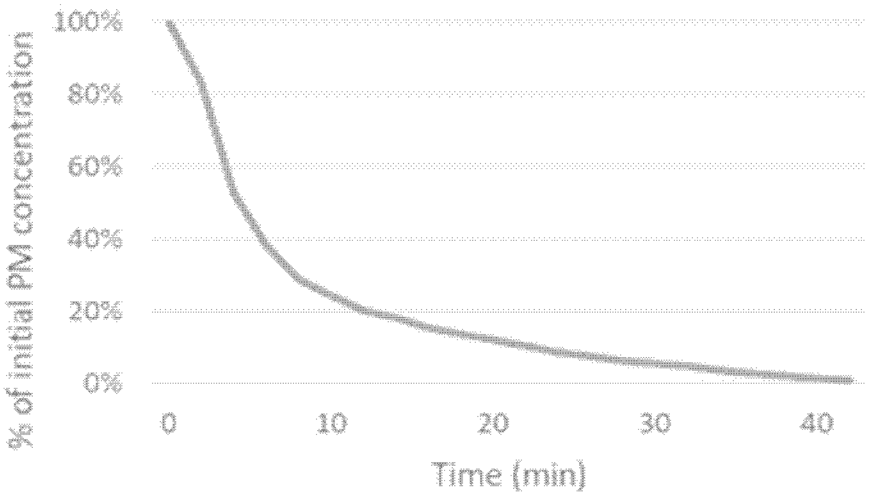

FIGS. 14A and 14B show the changes in percentage (%) in PM10 and PM2.5 concentrations respectively over time for the test conducted with Respirator 2. The results show that Respirator 2 achieves a PM removal efficiency of 97.60% for PM10 and 99.25% for PM2.5 at the end of the test.

The results above demonstrate that both example respirators have satisfactory PM removal efficiency but Respirator 2 is able to achieve a significantly higher PM removal efficiencies compared to Respirator 1 for both PM10 and PM2.5.

Example 9: Volatile Organic Compounds (VOC) Removal Efficiency

To evaluate and compare the Volatile Organic Compounds (VOC) removal efficiencies of the testing specimens (Respirators 1 and 2) with different structural arrangements as described in Example 6 above, a test for VOC removal efficiency was performed.

Materials and Methods

Instrument: Honeywell ppbRAE 3000

Environmental conditions: 25° C., around 50% Relative Humidity (RH)

Test Standard and Methods:

The test was conducted in a confined test chamber with a volume of 1 $m^3$. Acetone was utilized as a surrogate source of air pollutant. Acetone is a very volatile organic chemical, making it a good material for testing air cleaner performance on gaseous phase pollutants.

The test method is modified from test standard GB/T 18801-2015, which principally follows the test procedures outlined in GB/T 18801-2015 with the exception that a 1 $m^3$ confined chamber, different concentration/type of target pollutant, and longer testing times were used in the test. Under the modified method, an initial concentration of around 5 ppm of acetone vapor was maintained. Similar procedures were then performed to determine the "natural decay" and "total air cleaning" performances, respectively, and the measurements were conducted over 1 hour in this case. Finally, proper subtraction of the measurement of "natural decay" from the measurement of "total air cleaning" obtained would reveal the reported removal efficiency resulted from the standalone action of cleaning operation of the testing specimens.

Figure 15:
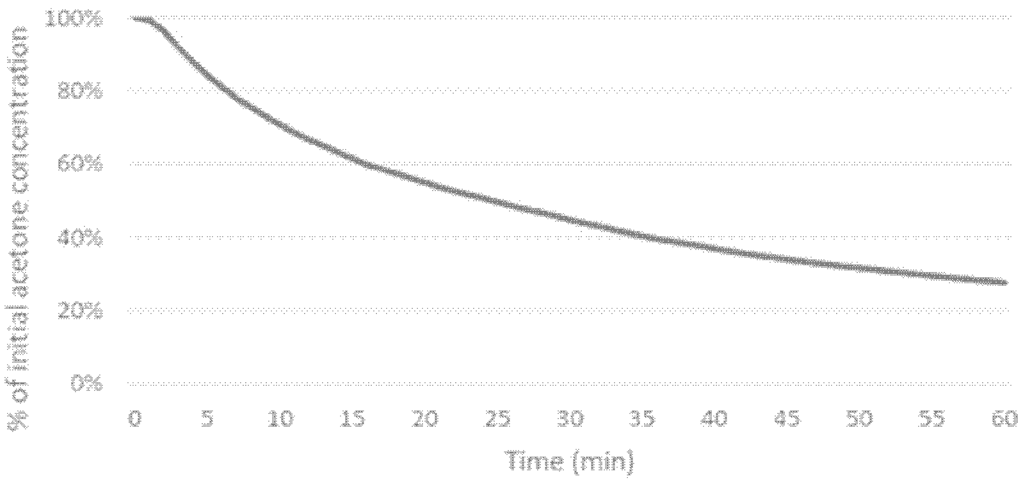
FIG. 15 is a chart showing the changes in percentage (%) in Acetone concentrations over time for the tests conducted with Respirator 1 in accordance with the same example embodiment as illustrated in FIGS. 13A and 13B.

Results:

FIG. 15 shows the changes in percentage (%) in Acetone concentration over time for the test conducted with Respirator 1. The results show that Respirator 1 achieved a maximum Acetone removal efficiency of 72.76%.

Figure 16:
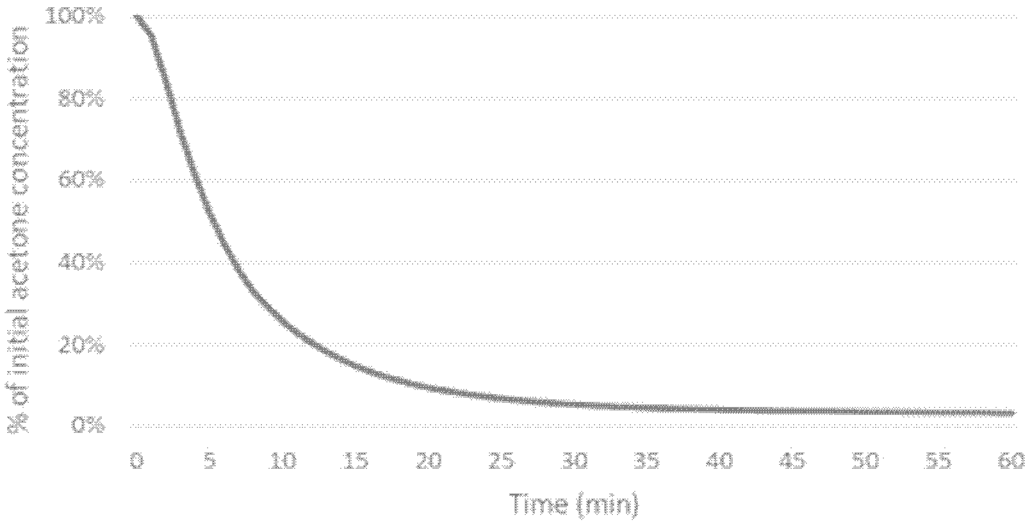
FIG. 16 is a chart showing the changes in percentage (%) in Acetone concentrations over time for the tests conducted with Respirator 2 in accordance with the same example embodiment as illustrated in FIGS. 14A and 14B.

FIG. 16 shows the changes in percentage (%) in Acetone concentration over time for the test conducted with Respirator 2. The results show that Respirator 2 achieved a maximum Acetone removal efficiency of 96.77%.

The results above demonstrate that both example respirators have satisfactory VOC removal efficiency but Respirator 2 is able to achieve a significantly higher VOC (e.g., Acetone) removal efficiency compared to Respirator 1.

Example 10: Germs Removal Efficiency

To evaluate the germ removal ability and efficiency of one of the testing specimens (Respirator 2) as described in Example 6 above, a test for germ removal efficiency was performed.

Materials and Methods

Test standard and method: GB 21551.3-2010 Appendix A

The tests were conducted with two identical chambers (i.e., a test chamber and a control chamber) having a standard volume of 3 $m^3$. *Staphylococcus albus, Staphylococcus aureus*, and *E. coli* were utilized as the test bacteria, as prepared respectively in form of a suspension with appropriate culture broth.

The test is designed to measure the test specimen standalone ability in removing target bacteria from air. Briefly, the test method includes the following steps: applying fixed amounts of the pure test strain to both the test and control chambers by means of a nebulizer, running the air purifier in the test chamber (leaving the control chamber to stand) for 120 mins, and quantifying the CFUs of cells before and after the test for both the chambers. The test is repeated for three times in total unless otherwise specified. After subtraction of the "natural decay" rate, the arithmetic mean of the three results obtained is taken to yield the final result.

Results:

Table 6 summarizes the removal efficiency (represented by removal rate (%)) of the three test bacteria (*Staphylococcus albus, Staphylococcus aureus* and *E. coli*) by Respirator 2.

TABLE 6

Germs removal rates of Respirator 2

| Test Bacteria | Replicate No. | Removal Rate (%) |
|---|---|---|
| *Staphylococcus albus* (8032) | 1 | 99.90 |
| | 2 | 99.90 |
| | 3 | 99.90 |
| | Average | 99.90 |
| *Staphylococcus aureus* (ATCC 6538) | 1 | 99.92 |
| | 2 | 99.90 |
| | 3 | 99.91 |
| | Average | 99.91 |
| *E. coli* (8099) | 1 | 99.91 |
| | 2 | 99.94 |
| | 3 | 99.95 |
| | Average | 99.93 |

The results above demonstrate that Respirator 2 achieves an outstanding removal rates of around 99.90% to 99.93% of the test bacteria, indicating that Respirator 2 is highly effective in removing various germs such as bacteria.

Example 11: User Experience Study

To investigate the user's experience with the testing specimens (Respirator 1 and 2) as described in Example 6 above and to optimize the design of the respirator, a study on the user experience in using the testing specimens was performed.

Materials and Methods

Subjects:

15 drainage workers were invited to conduct two independent trials on the testing specimens (Respirators 1 and 2). They were requested to wear the respirators to experience their function and design, while performing their job duties normally in an indoor environment. A total of 30 specimens (15 units of Respirator 1 and 15 units of Respirator 2) were deployed in two batches for the trials.

Methods:

After the trials, user experience questionnaires were distributed to collect the data and feedbacks from the subjects (also referred to as "the users"). In this example, the user experience questionnaire included the questions as listed below:

Question 1: Without wearing the respirator, I found the smell very strong.

Question 2: After putting on the respirator, I found the smell weaker. I am happy with its odor removal ability.

Question 3: The face mask has satisfactory comfort and softness.

Question 4: The product has good lifetime of battery I expect it to have.

Question 5: I am satisfied with the size and weight of the product when carrying it.

Question 6: I am satisfied with the positive pressure airflow design in the respirator.

Question 7: I found the product is easy to use and the control interface is user-friendly.

Question 8: I found the procedure for cleaning/replacing the filter is easy and fast.

For each trial, users were requested to provide their feedback on each question above by providing a score with a scale of 1 (strongly disagree) to 5 (strongly agree). A score of 3 or above is considered as "agree" by the users. The scores of all subjects on each question were collected to calculate the average score accordingly.

Figure 17:
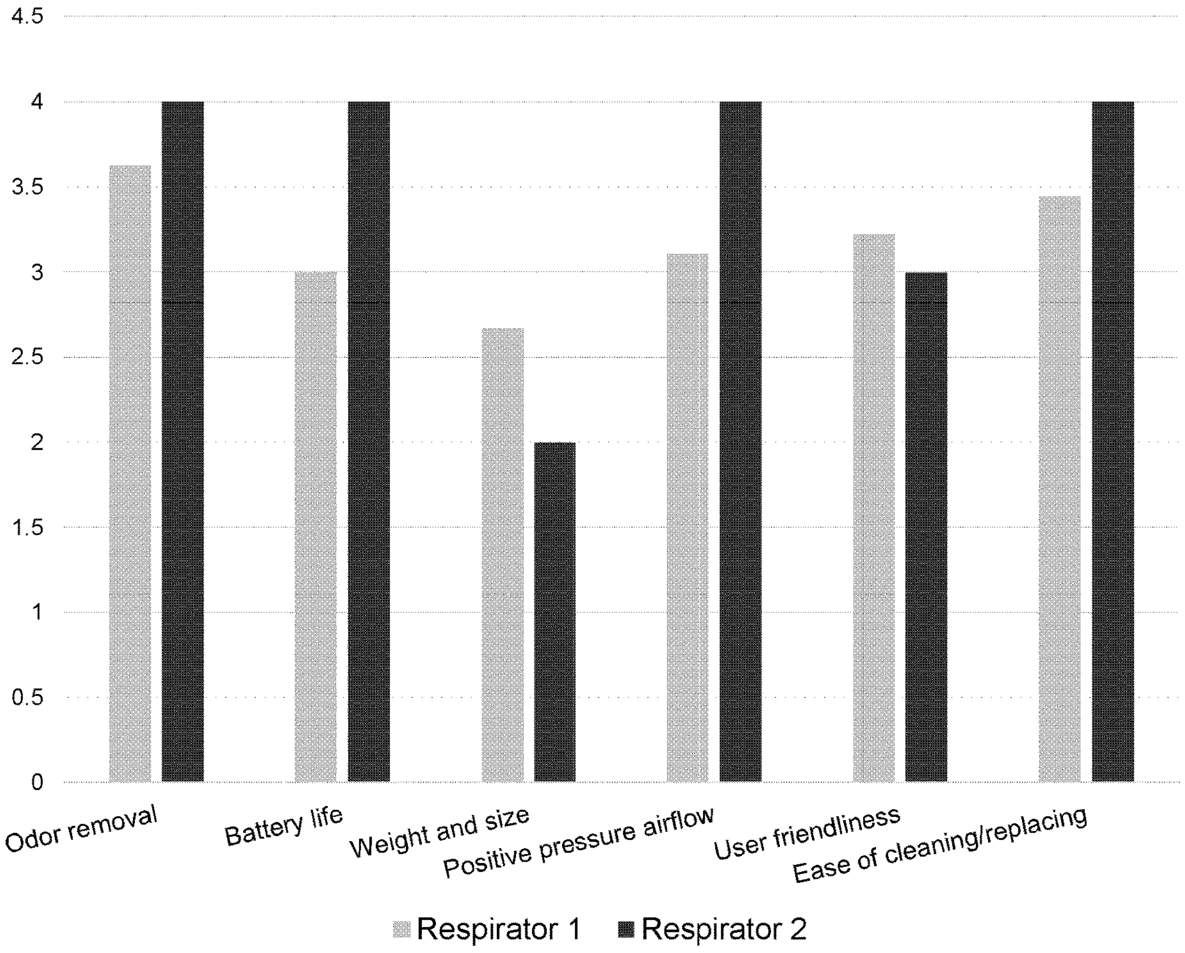
FIG. 17 is a bar chart showing a comparison of the average scores of Respirator 1 and Respirator 2 on different aspects of user experience in accordance with the same example embodiment as illustrated in FIGS. 13A, 13B, 14A and 14B.

Results:

FIG. 17 shows a comparison of the average score of Respirator 1 and Respirator 2 in different aspects of user experience, including "odor removal" (corresponds to question 2), "battery life" (corresponds to question 4), "weight and size" (corresponds to question 5), "positive pressure airflow" (corresponds to question 6), "user friendliness" (corresponds to question 7) and "ease of cleaning/replacing" (corresponds to question 8).

Overall, a significantly large percentage of users found that both respirators used in the trial is useful and satisfied with its performances irrespective of whether it is Respirator 1 or Respirator 2. Compared to Respirator 1, users are more satisfied with the performances of Respirator 2 in almost all aspects, except in terms of weight and size of the respirator.

On the aspect of "odor removal" ability, the average score for Respirator 2 (average score of 4) is higher compared to Respirator 1 (average score of 3.625), indicating that the improvements in the VOC removal ability and the air inflow and outflow rates in Respirator 2 can lead to better performance and user experience.

On the aspect of satisfaction of "positive pressure airflow" design, the average score for Respirator 2 (average score of 4) is higher compared to Respirator 1 (average score of 3.11). This may be at least attributed to the improvements in the air inflow and outflow rates in Respirator 2 which lead to better user experience.

On the aspect of "battery life", a majority of users are able to have enough battery life of the testing specimens to last for their work hours. The average score for Respirator 2 (average score of 4) is higher compared to Respirator 1 (average score of 3). This may be at least attributed to the improvements in battery utility of the Respirator 2.

On the aspect of "ease of cleaning/replacing", the average score for Respirator 2 (average score of 4) is higher compared to Respirator 1 (average score of 3.45), indicating that the arrangement of the removable filter case in Respirator 2 is more acceptable to users.

Now turning to FIGS. 18A-18G, which shows the distribution of scores by the users on different aspects of performance of Respirator 2 in the trial.

Figure 18A:
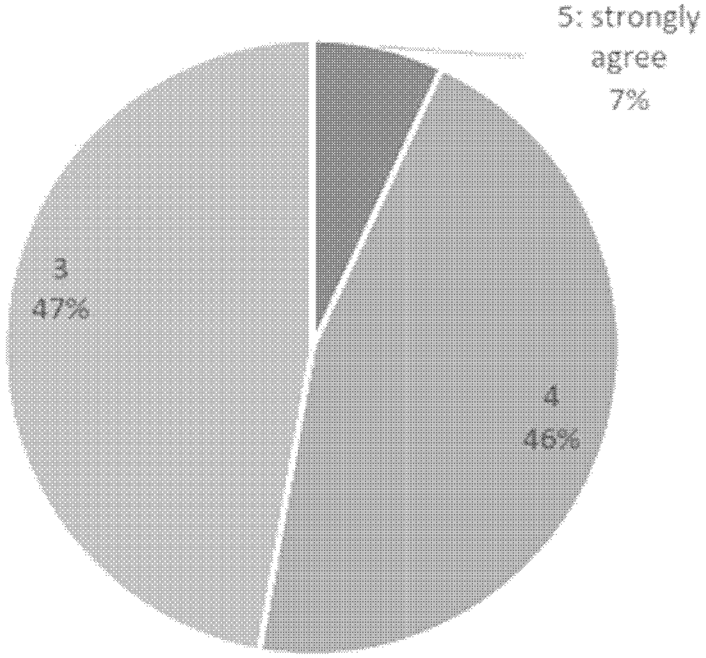
FIG. 18A is a pie chart showing the distribution of scores by the users on the aspect of odor removal ability of Respirator 2 in accordance with the same example embodiment as illustrated in FIGS. 14A and 14B.

FIG. 18A shows the distribution of scores by the users on the aspect of odor removal ability of Respirator 2 (corresponds to question 2). All users generally agreed with the odor removal ability of Respirator 2, as no negative feedbacks (score of 2 or below) were received. More than 50% of the users even showed a high degree of satisfaction (score of 4 or 5) with the odor removal ability of Respirator 2.

Figure 18B:
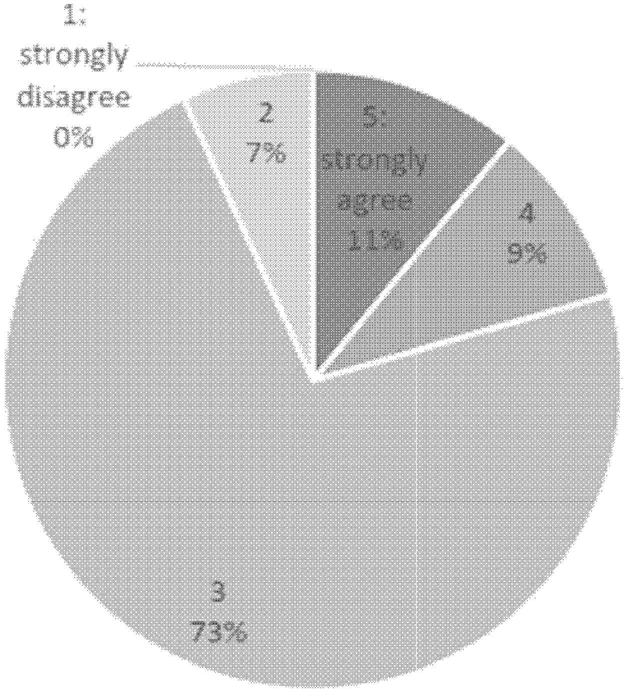
FIG. 18B is a pie chart showing the distribution of scores by the users on the aspect of comfort and softness of the face mask of Respirator 2 in accordance with the same example embodiment as illustrated in FIGS. 14A and 14B.

FIG. 18B shows the distribution of scores by the users on the aspect of comfort and softness of the face mask of Respirator 2 (corresponds to question 3). A large majority (73%) of users agreed with this aspect, with around 20% of the users showing a high degree of satisfaction (score of 4 or 5) and only around 7% found slightly uncomfortable.

Figure 18C:
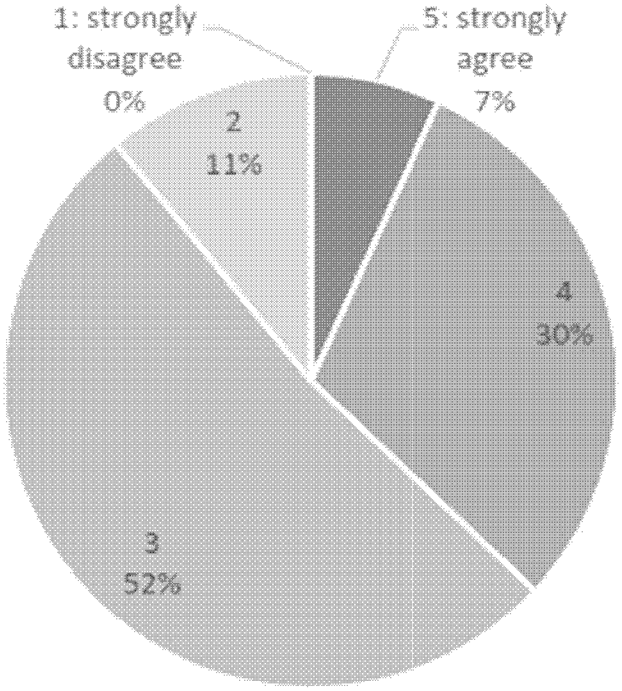
FIG. 18C is a pie chart showing the distribution of scores by the users on the aspect of battery life of Respirator in accordance with the same example embodiment as illustrated in FIGS. 14A and 14B.
Figure 18D:
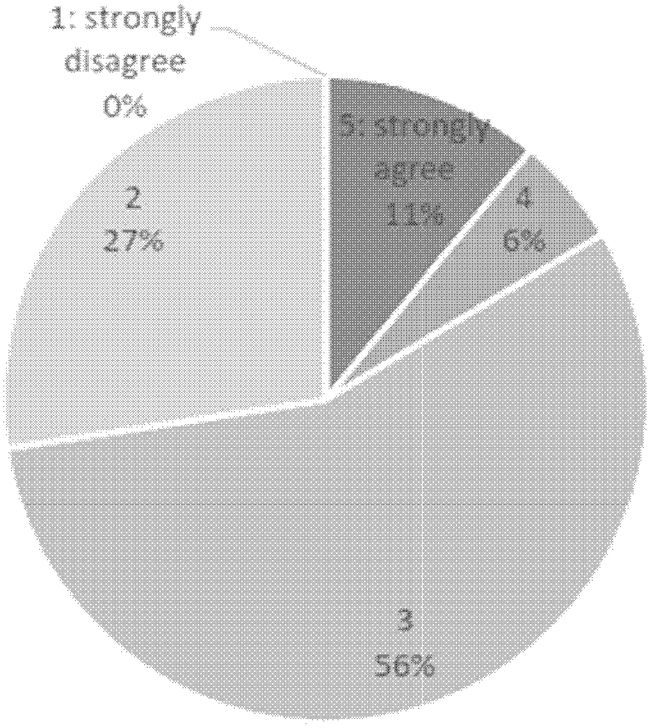
FIG. 18D is a pie chart showing the distribution of scores by the users on the aspect of size and weight of Respirator 2 in accordance with the same example embodiment as illustrated in FIGS. 14A and 14B.

FIG. 18C shows the distribution of scores by the users on the aspect of satisfaction of battery life of Respirator 2 (corresponds to question 4). Most (around 90%) of users agreed with this aspect, with around 40% of the users showing a high degree of satisfaction (score of 4 or 5) and only around 11% found the battery life unsatisfactory. This indicates that the performance/capacity of the battery is good enough to last the duration of the users' work time.

Figure 18E:
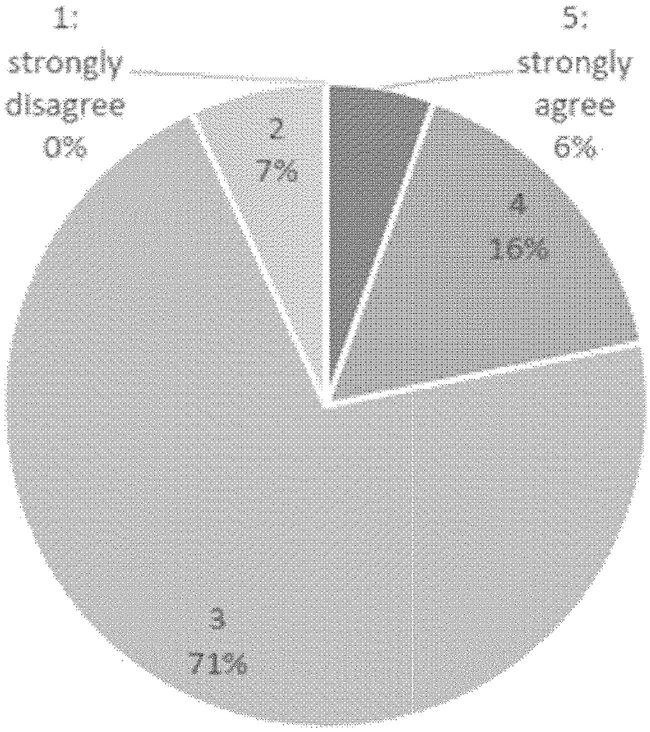
FIG. 18E is a pie chart showing the distribution of scores by the users on the aspect of positive pressure airflow design of Respirator 2 in accordance with the same example embodiment as illustrated in FIGS. 14A and 14B.

FIG. 18E shows the distribution of scores by the users on the aspect of satisfaction of positive pressure airflow design of Respirator 2 (corresponds to question 6). Most (93%) of users agreed with this aspect, with around 20% of the users showing a high degree of satisfaction (score of 4 or 5), indicating that most users were not bothered by the positive pressure airflow of the respirator and the design was acceptable to the users.

Figure 18F:
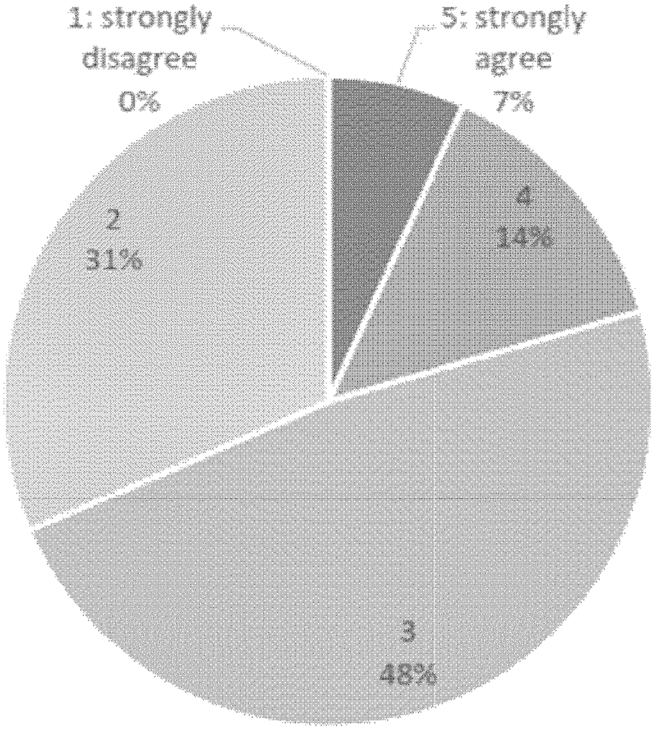
FIG. 18F is a pie chart showing the distribution of scores by the users on the aspect of ease of use and user friendliness of control interface of Respirator 2 in accordance with the same example embodiment as illustrated in FIGS. 14A and 14B.

FIG. 18F shows the distribution of scores by the users on the aspect of ease of use and user-friendliness of control interface of Respirator 2 (corresponds to question 7). A large majority (around 70%) of users agreed with this aspect, with around 20% of the users showing a high degree of satisfaction (score of 4 or 5), indicating that the majority of users found that the respirator is easy to operate.

Figure 18G:
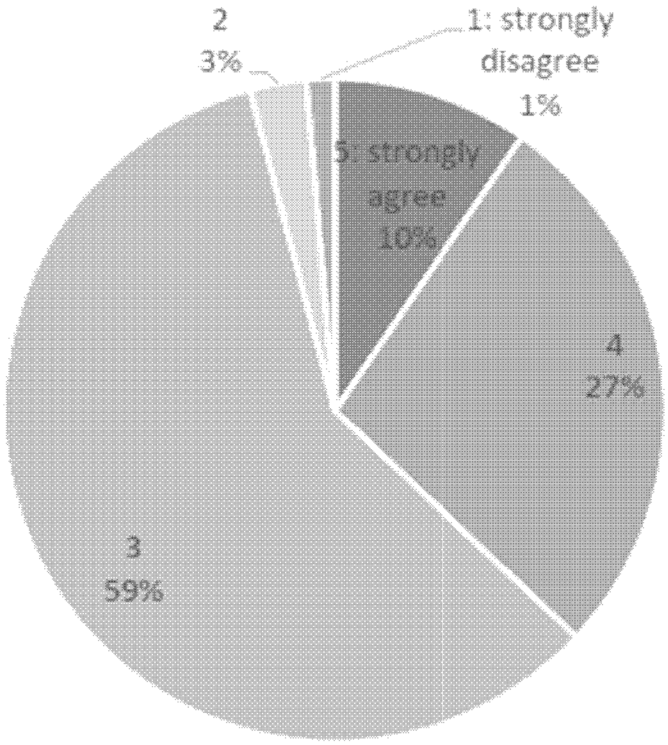
FIG. 18G is a pie chart showing the distribution of scores by the users on the aspect of procedure for cleaning or replacing the filter of Respirator 2 in accordance with the same example embodiment as illustrated in FIGS. 14A and 14B.

FIG. 18G shows the distribution of scores by the users on the aspect of ease of cleaning and replacing the filter of Respirator 2 (corresponds to question 8). An overwhelming majority (96%) of users agreed with this aspect, with around 40% of the users showing a high degree of satisfaction (score of 4 or 5). This may be attributed to the design of the removal filter case of Respirator 2, which makes it easy and efficient to remove the used filter case and replace it with a new one.

The methods and apparatus in accordance with example embodiments are provided as examples, and examples from one method or apparatus should not be construed to limit examples from another method or apparatus. Further, methods and apparatus discussed within different figures can be added to or exchanged with methods and apparatus in other figures.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A respirator, comprising i) a face mask;

ii) a removable filter case comprising at least one filter; wherein each of the at least one filter is a porous filter comprising a filtration material;

iii) an air flow system in fluid communication with the removable filter case and the face mask, comprising (a) an enclosed container; and (b) a blower housed within the enclosed container, wherein the air flow system is configured to generate a flow of air such that ambient air passes through the porous filter to the face mask; and iv) an oxidant generator configured to produce at least one oxidant;

wherein at least one contaminant in the flow of air is adsorbed by the porous filter, and the filtration material catalyzes an oxidation reaction between the at least one oxidant and the at least one contaminant to promote decomposition of the at least one contaminant on the porous filter.

2. The respirator of claim 1, wherein the oxidant generator is positioned before the porous filter along the direction of the flow of air.

3. The respirator of claim 1, wherein the filtration material has a pore size that permits adsorption of the at least one contaminant and the at least one oxidant.

4. The respirator of claim 1, wherein the filtration material comprises zeolite having a pore size in the range of 2 Angstroms to 20 Angstroms.

5. The respirator of claim 1, wherein the respirator further comprises a mechanical filter positioned before the porous filter along the direction of the flow of air.

6. The respirator of claim 5, wherein the mechanical filter is a high-efficiency particulate air (HEPA) filter.

7. The respirator of claim 1, wherein the oxidant generator is an ozone generator and the at least one oxidant is ozone.

8. The respirator of claim 1, wherein the air flow system further comprises a tube connecting the enclosed container to the face mask, such that the flow of air passes through the tube.

9. The respirator of claim 8, wherein the face mask comprises a mask inlet valve and a mask outlet valve, wherein the tube connects the enclosed container to the face mask through the mask inlet valve, and the mask inlet valve is configured for a one-way flow of air into the face mask.

10. The respirator of claim 9, wherein the air flow system further comprises a second tube connecting the face mask to the enclosed container, and the mask outlet valve of the face mask is connected to the second tube and configured for a one-way flow of air out of the face mask.

* * * * *